US010022130B2

(12) United States Patent
Edwards et al.

(10) Patent No.: US 10,022,130 B2
(45) Date of Patent: Jul. 17, 2018

(54) POLYMER 4-IN-1 FEMORAL CUTTING BLOCK

(71) Applicant: DEPUY IRELAND UNLIMITED COMPANY, Co Cork OT (IE)

(72) Inventors: Jon M. Edwards, Warsaw, IN (US); Michael J. Rock, Leeds (GB); Chad S. McAlexander, Fort Wayne, IN (US)

(73) Assignee: DePuy Ireland Unlimited Company (IE)

( * ) Notice: Subject to any disclaimer, the term of this patent is extended or adjusted under 35 U.S.C. 154(b) by 261 days.

(21) Appl. No.: 14/092,302

(22) Filed: Nov. 27, 2013

(65) Prior Publication Data

US 2014/0257305 A1    Sep. 11, 2014

Related U.S. Application Data

(63) Continuation-in-part of application No. 13/785,287, filed on Mar. 5, 2013.

(51) Int. Cl.
*A61B 17/15* (2006.01)

(52) U.S. Cl.
CPC ............ *A61B 17/154* (2013.01); *A61B 17/15* (2013.01); *A61B 17/155* (2013.01)

(58) Field of Classification Search
None
See application file for complete search history.

(56) References Cited

U.S. PATENT DOCUMENTS 5,129,909 A * 7/1992 Sutherland ........... A61B 17/155
606/53
5,178,621 A * 1/1993 Cook ................. A61B 17/1703
606/104

(Continued)

FOREIGN PATENT DOCUMENTS

EP    2039304 A2    3/2009
EP    2208469 A1    7/2010

(Continued)

OTHER PUBLICATIONS

European Search Report for European Application No. 14157968.0-1654, dated May 15, 2014, 5 pages.

(Continued)

*Primary Examiner* — Matthew Lawson
*Assistant Examiner* — Amy Sipp
(74) *Attorney, Agent, or Firm* — Barnes & Thornburg LLP

(57) ABSTRACT

An orthopedic surgical instrument including a polymer 4-in-1 femoral cutting block having a chamfer cutting slot defined therein, and a chamfer cutting guide assembly secured within the chamfer cutting slot. The chamfer cutting guide assembly includes a first planar surface, a second planar surface spaced apart from, and extending parallel to, the first planar surface, a third planar surface connected to the second planar surface and extending at an angle relative to the first planar surface and a fourth planar surface connected to the first planar surface and extending parallel to the third planar surface. The first planar surface and the second planar surface define a first metallic planar cutting guide, and the third planar surface and the fourth planar surface define a second metallic planar cutting guide. The chamfer cutting guide assembly may include a pair of metallic bushings.

20 Claims, 14 Drawing Sheets

(56) References Cited

U.S. PATENT DOCUMENTS

| | | | |
|---|---|---|---|
| 5,403,321 A * | 4/1995 | DiMarco | A61B 17/1721 606/96 |
| 5,683,397 A * | 11/1997 | Vendrely | A61B 17/155 606/88 |
| 5,716,361 A | 2/1998 | Masini | |
| 7,967,824 B2 | 6/2011 | Thau et al. | |
| 2005/0209605 A1 | 9/2005 | Grimm et al. | |
| 2005/0228393 A1 | 10/2005 | Williams, III et al. | |
| 2007/0213738 A1 * | 9/2007 | Martin | A61B 17/155 606/87 |
| 2008/0154269 A1 * | 6/2008 | Roger | A61B 17/155 606/88 |
| 2008/0221569 A1 * | 9/2008 | Moore | A61B 17/15 606/53 |
| 2009/0222014 A1 * | 9/2009 | Bojarski | A61B 17/155 606/88 |
| 2010/0168752 A1 | 7/2010 | Edwards | |
| 2010/0168753 A1 * | 7/2010 | Edwards | A61B 17/155 606/88 |
| 2010/0191244 A1 * | 7/2010 | White | A61B 17/155 606/88 |
| 2013/0325017 A1 * | 12/2013 | Lomicka | A61B 17/15 606/87 |

FOREIGN PATENT DOCUMENTS

| | | |
|---|---|---|
| EP | 2319433 A1 | 5/2011 |
| WO | 2012024317 A2 | 2/2012 |

OTHER PUBLICATIONS

SIGMA Fixed Reference Surgical Technique by DePuy Orthopaedics, Inc. (2010).

Australian Examination Report No. 1 issued in connection with Australian Application No. 2014201030, dated Dec. 9, 2017, 4 pages.

* cited by examiner

POLYMER 4-IN-1 FEMORAL CUTTING BLOCK

This application is a continuation-in-part and claims priority to U.S. patent application Ser. No. 13/785,287, which was filed on Mar. 5, 2013 and is expressly incorporated herein by reference.

TECHNICAL FIELD

The present disclosure relates generally to orthopaedic surgical instruments and, more particularly, to surgical instruments used to resect a patient's bone.

BACKGROUND

Joint arthroplasty is a well-known surgical procedure by which a diseased and/or damaged natural joint is replaced by a prosthetic joint. Typical artificial joints include knee prostheses, hip prostheses, shoulder prostheses, ankle prostheses, and wrist prostheses, among others. To facilitate the replacement of the natural joint with the prosthesis, orthopaedic surgeons use a variety of orthopaedic surgical instruments such as, for example, saws, drills, reamers, rasps, broaches, cutting blocks, drill guides, milling guides, and other surgical instruments.

SUMMARY

According to one aspect of the disclosure, an orthopaedic surgical instrument includes a polymer 4-in-1 femoral cutting block having a chamfer cutting slot defined therein. A first metallic planar cutting guide is secured within the chamfer cutting slot of the polymer 4-in-1 femoral cutting block. A second metallic planar cutting guide is also secured within the chamfer cutting slot of the polymer 4-in-1 femoral cutting block. The second metallic planar cutting guide is arranged at an oblique angle relative to, and spaced apart from, the first metallic planar cutting guide. A first metallic bushing is secured within the chamfer cutting slot of the polymer 4-in-1 femoral cutting block, with an outer surface of the first metallic bushing being positioned at a lateral end of each of the first and second metallic planar cutting guides. A second metallic bushing is also secured within the chamfer cutting slot of the polymer 4-in-1 femoral cutting block, with the outer surface of the second metallic bushing being positioned at a medial end of each of the first and second metallic planar cutting guides.

The outer surface of the first metallic bushing may be spaced apart laterally from the lateral end of each of the first and second metallic planar cutting guides, or may be positioned in contact with the lateral end of each of the first and second metallic planar cutting guides. Likewise, the outer surface of the second metallic bushing may be spaced apart medially from the medial end of each of the first and second metallic planar cutting guides, or positioned in contact with the medial end of each of the first and second metallic planar cutting guides.

Each of the first and second metallic bushings may be embodied as cylindrically-shaped bushings having an elongated bore extending therethrough.

In an embodiment, the second metallic planar cutting guide is spaced apart from the first metallic planar cutting guide in the anterior/posterior direction.

The orthopaedic surgical instrument may also include a third metallic planar cutting guide secured within the chamfer cutting slot of the polymer 4-in-1 femoral cutting block, and a fourth metallic planar cutting guide secured within the chamfer cutting slot of the polymer 4-in-1 femoral cutting block. The fourth metallic planar cutting guide may be arranged at an oblique angle relative to the third metallic planar cutting guide.

The polymer 4-in-1 femoral cutting block may also have an anterior cutting slot defined therein. The anterior cutting slot is spaced apart anteriorly from the chamfer cutting slot, and has a metallic anterior cutting guide secured within it.

Moreover, the polymer 4-in-1 femoral cutting block may also have a posterior cut surface defined therein. The posterior cut surface is spaced apart posteriorly from the chamfer cutting slot, and has a metallic posterior cutting guide secured to it.

According to another aspect, an orthopaedic surgical instrument includes a polymer 4-in-1 femoral cutting block having a chamfer cutting slot defined therein, and a metallic captured chamfer cutting guide assembly secured within the chamfer cutting slot. The metallic captured chamfer cutting guide assembly includes a first metallic planar cutting guide and a second metallic planar cutting guide arranged at an oblique angle relative to, and spaced apart from, the first metallic planar cutting guide. The metallic captured chamfer cutting guide assembly also includes a first metallic bushing having its outer surface positioned at a lateral end of each of the first and second metallic planar cutting guides, and a second metallic bushing having its outer surface positioned at a medial end of each of the first and second metallic planar cutting guides.

The outer surface of the first metallic bushing may be spaced apart laterally from the lateral end of each of the first and second metallic planar cutting guides, or may be positioned in contact with the lateral end of each of the first and second metallic planar cutting guides. Likewise, the outer surface of the second metallic bushing may be spaced apart medially from the medial end of each of the first and second metallic planar cutting guides, or positioned in contact with the medial end of each of the first and second metallic planar cutting guides.

Each of the first and second metallic bushings may be embodied as cylindrically-shaped bushings having an elongated bore extending therethrough.

In an embodiment, the second metallic planar cutting guide is spaced apart from the first metallic planar cutting guide in the anterior/posterior direction.

The orthopaedic surgical instrument may also include a third metallic planar cutting guide secured within the chamfer cutting slot of the polymer 4-in-1 femoral cutting block, and a fourth metallic planar cutting guide secured within the chamfer cutting slot of the polymer 4-in-1 femoral cutting block. The fourth metallic planar cutting guide may be arranged at an oblique angle relative to the third metallic planar cutting guide.

The polymer 4-in-1 femoral cutting block may also have an anterior cutting slot defined therein. The anterior cutting slot is spaced apart anteriorly from the chamfer cutting slot, and has a metallic anterior cutting guide secured within it.

Moreover, the polymer 4-in-1 femoral cutting block may also have a posterior cut surface defined therein. The posterior cut surface is spaced apart posteriorly from the chamfer cutting slot, and has a metallic posterior cutting guide secured to it.

According to another aspect, an orthopaedic surgical instrument includes a polymer cutting block having a cutting slot defined therein, and a metallic captured cutting guide assembly secured within the cutting slot. The captured metallic chamfer cutting guide assembly may include a first metallic planar cutting guide, and a second metallic planar cutting guide spaced apart from the first metallic planar cutting guide. The captured metallic chamfer cutting guide assembly may also include a first metallic bushing having an outer surface thereof positioned at a first end of each of the first and second metallic planar cutting guides, and a second metallic bushing having an outer surface thereof positioned at a second end of each of the first and second metallic planar cutting guides.

Each of the first and second metallic bushings may be embodied as cylindrically-shaped bushings having an elongated bore extending therethrough.

In an embodiment, the second metallic planar cutting guide is spaced apart from the first metallic planar cutting guide in the anterior/posterior direction.

According to another aspect, an orthopaedic surgical instrument includes a polymer 4-in-1 femoral cutting block having a chamfer cutting slot defined therein, and a first metallic planar cutting guide secured within the chamfer cutting slot. The first metallic planar cutting guide is defined by a first planar surface and a second planar surface spaced apart from, and extending parallel to, the first planar surface. A second metallic planar is cutting guide secured within the chamfer cutting slot. The second metallic planar cutting guide is defined by a third planar surface extending at an oblique angle relative to the first planar surface, and a fourth planar surface extending parallel to, spaced apart from, the third planar surface. A first metallic bushing is secured within the chamfer cutting slot of the polymer 4-in-1 femoral cutting block, and an outer surface of the first metallic bushing is positioned at a lateral end of each of the first and second metallic planar cutting guides. A second metallic bushing is secured within the chamfer cutting slot of the polymer 4-in-1 femoral cutting block, and an outer surface of the second metallic bushing is positioned at a medial end of each of the first and second metallic planar cutting guides.

In some embodiments, the fourth planar surface may be connected to, and extend at an oblique angle relative to, the first planar surface. The second planar surface may be connected to, and extend at an oblique angle relative to, the third planar surface. Additionally, in some embodiments, the first planar surface may be spaced apart from the third planar surface in an anterior/posterior direction.

In some embodiments, the orthopaedic surgical instrument may include a third metallic planar cutting guide secured within the chamfer cutting slot of the polymer 4-in-1 femoral cutting block, and a fourth metallic planar cutting guide secured within the chamfer cutting slot of the polymer 4-in-1 femoral cutting block. The fourth metallic planar cutting guide may be arranged at an oblique angle relative to the third metallic planar cutting guide. In some embodiments, the third metallic planar cutting guide may extend parallel to the first metallic planar cutting guide, and the fourth metallic planar cutting guide may extend parallel to the second metallic planar cutting guide.

Additionally, in some embodiments, the polymer 4-in-1 femoral cutting block may further have an anterior cutting slot defined therein. The anterior cutting slot may be spaced apart anteriorly from the chamfer cutting slot. A metallic anterior cutting guide may be secured within the anterior cutting slot of the polymer 4-in-1 femoral cutting block.

In some embodiments, the polymer 4-in-1 femoral cutting block may have a posterior cut surface defined therein. The posterior cut surface may be spaced apart posteriorly from the chamfer cutting slot. A metallic posterior cutting guide may be secured to the posterior cut surface of the polymer 4-in-1 femoral cutting block.

In some embodiments, the orthopaedic surgical instrument may include a metallic rod spaced apart from the first planar surface such that an opening is defined therebetween. The metallic rod may extend in a medial-lateral direction. Additionally, in some embodiments, the orthopaedic surgical instrument may include a second metallic rod spaced apart from the third planar surface such that a second opening is defined therebetween. The second metallic rod may extend in the medial-lateral direction.

According to another aspect, an orthopaedic surgical instrument includes a polymer 4-in-1 femoral cutting block having a chamfer cutting slot defined therein, and a chamfer cutting guide assembly secured within the chamfer cutting slot. The chamfer cutting guide assembly includes a first planar surface, a second planar surface spaced apart from, and extending parallel to, the first planar surface, a third planar surface connected to the second planar surface and extending at an oblique angle relative to the first planar surface and a fourth planar surface connected to the first planar surface and extending parallel to the third planar surface. The first planar surface and the second planar surface define a first metallic planar cutting guide, and the third planar surface and the fourth planar surface define a second metallic planar cutting guide arranged at an oblique angle relative to, and spaced apart from, the first metallic planar cutting guide.

In some embodiments, the orthopaedic surgical instrument may include a first metallic bushing having an outer surface thereof positioned at a lateral end of each of the first and second metallic planar cutting guides, and a second metallic bushing having an outer surface thereof positioned at a medial end of each of the first and second metallic planar cutting guides. Additionally, in some embodiments, the outer surface of the first metallic bushing may be spaced apart laterally from the lateral ends of the first and second metallic planar cutting guides, and the outer surface of the second metallic bushing may be spaced apart medially from the medial ends of the first and second metallic planar cutting guides.

In some embodiments, the outer surface of the first metallic bushing may be in contact with the lateral ends of the first and second metallic planar cutting guides, and the outer surface of the second metallic bushing may be in contact with the medial ends of the first and second metallic planar cutting guides.

In some embodiments, each of the first and second metallic bushings may include a cylindrically-shaped bushing having an elongated bore extending therethrough.

In some embodiments, the first planar surface may be spaced apart from the third planar surface in an anterior/posterior direction.

Additionally, in some embodiments, the chamfer cutting guide assembly may further include a fifth planar surface positioned opposite the first planar surface in the chamfer cutting slot of the polymer 4-in-1 femoral cutting block. The fifth planar surface may be spaced apart from, and extend parallel relative to, the first planar surface such that the first planar surface, the second planar surface, and the fifth planar surface define the first metallic planar cutting guide.

In some embodiments, the chamfer cutting guide assembly may further include a sixth planar surface positioned opposite the third planar surface in the chamfer cutting slot of the polymer 4-in-1 femoral cutting block. The sixth planar surface may be spaced apart from, and extend parallel relative to, the third planar surface such that the third planar surface, the fourth planar surface, and the sixth planar surface define the second metallic planar cutting guide.

According to another aspect, an orthopaedic surgical instrument includes a polymer 4-in-1 femoral cutting block including a chamfer cutting slot, and a first metallic planar cutting guide secured within the chamfer cutting slot. The first metallic planar cutting guide extends through the chamfer cutting slot from a first end to a second end. A second metallic planar cutting guide is secured within the chamfer cutting slot, and the second metallic planar cutting guide is arranged at an oblique angle relative to, and spaced apart from, the first metallic planar cutting guide. The second metallic planar cutting guide extends from a first end positioned posterior of the first end of the first metallic planar cutting guide to a second end positioned anterior of the second end of the first metallic planar cutting guide.

The first metallic planar cutting guide is defined by a first metallic plate extending from the first end of the first metallic planar cutting guide to an inner end and a second metallic plate extending parallel to the first metallic plate and inwardly from the second end of the first metallic planar cutting guide to an inner end spaced apart from the inner end of the first metallic plate.

The second metallic planar cutting guide is defined by a third metallic plate connected to the inner end of the second metallic plate, and the third metallic plate extends from the inner end to the first end of the second metallic planar cutting guide.

In some embodiments, the second metallic planar cutting guide may be further defined by a fourth metallic plate connected to the inner end of the first metallic plate and extending outwardly, parallel to the third metallic plate, to the second end of the second metallic planar cutting guide.

In some embodiments, the first metallic planar cutting guide may be further defined by a fifth metallic plate extending parallel to, and spaced apart from, the first metallic plate and the second metallic plate, and the second metallic planar cutting guide may be further defined by a sixth metallic plate extending parallel to, and spaced apart from, the third metallic plate and the fourth metallic plate.

BRIEF DESCRIPTION OF THE DRAWINGS

The detailed description particularly refers to the following figures, in which.

DETAILED DESCRIPTION OF THE DRAWINGS

Figure 1:
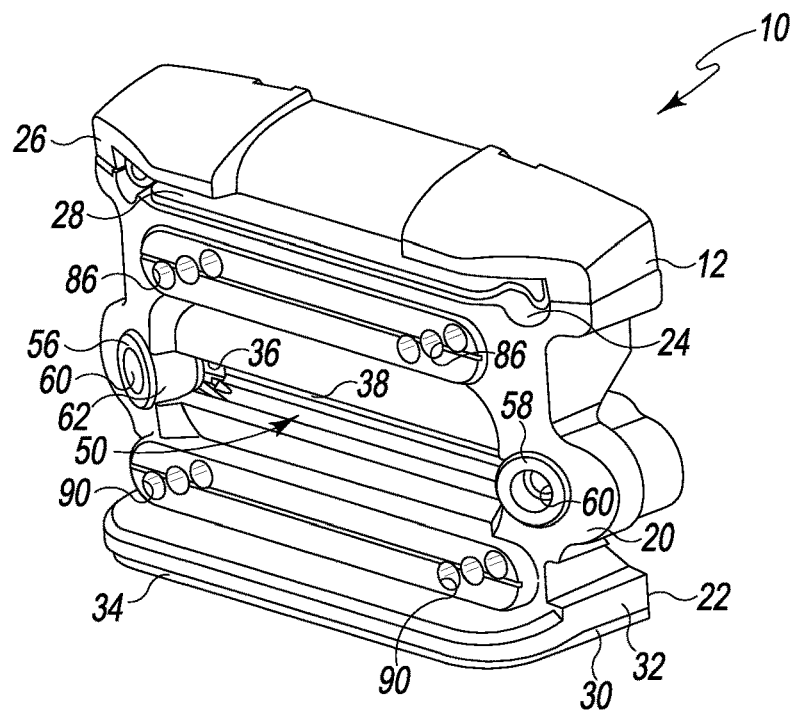
FIG. 1 is a perspective view of an orthopaedic surgical instrument.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring to FIGS. 1-4, one embodiment of a single use orthopaedic surgical instrument 10 is shown. As its name implies, the single use orthopaedic surgical instrument 10 is intended to be disposed of after use in a single orthopaedic procedure. In the illustrative embodiment described herein, the orthopaedic surgical instrument is embodied as a single use 4-in-1 cutting block 12 for use in the surgical preparation of the patient's distal femur during a knee replacement procedure. As will be discussed below in greater detail, a 4-in-1 cutting block 12 is used to perform four cuts on the patient's distal femur with the same block—an anterior cut, a posterior cut, and two chamfer cuts.

As a single use instrument, the 4-in-1 cutting block 12 may be formed from polymeric materials such as, for example, polyamide, polyphenylsulfone, or polyketone. In such an embodiment, the surfaces used to guide surgical instruments, such as cutting guide surfaces for guiding bone saws and bushings for guiding drills and surgical pins, are formed from a metallic material such as, for example, steel, titanium alloy, or cobalt chromium alloy. Such use of metallic components or "inserts" prevents the surgical tools from coming into contact with the polymeric materials of the block's body.

The metallic components described herein may be secured to the polymer 4-in-1 cutting block in a number of different manners. For example, the metallic components may be overmolded to the polymer cutting block or otherwise secured to it as part of the molding process of the block.

The metallic components may also be welded to the cutting block or secured to it with an adhesive. Other methods of securing the metallic components may also be employed.

The 4-in-1 cutting block 12 includes an outer surface 20 and a bone-engaging surface 22 positioned opposite the outer surface 20. The 4-in-1 cutting block 12 has an anterior cutting slot 24 formed near its anterior end 26. The anterior cutting slot 24 is an elongated slot extending in the medial/lateral direction. The anterior cutting slot 24 extends through the entire thickness of the 4-in-1 cutting block 12—that is, the anterior cutting slot 24 extends from the cutting block's outer surface 20 to its bone-engaging surface 22 thereby being open to both surfaces. A metallic anterior cutting guide 28 is secured within the anterior cutting slot 24 of the polymer 4-in-1 cutting block 12. The anterior cutting guide 28 lines the anterior cutting slot 24 and is embodied as a captured cutting guide (i.e., it is closed on all sides so as to capture a saw blade therein), although the cutting block 12 and the cutting guide 28 may alternatively be embodied as a non-captured cutting guide. The anterior cutting guide 28 is sized and shaped to receive the blade (see FIG. 6) of a surgical saw or other cutting instrument and orient the blade to resect the anterior surface of the patient's femur during an orthopaedic surgical procedure.

The 4-in-1 cutting block 12 has a posterior cutting surface 30 formed near its posterior end 32. The posterior cutting surface 30 is an elongated surface extending in the medial/lateral direction. The posterior cutting surface 30 extends the entire thickness of the 4-in-1 cutting block 12—that is, it extends from the cutting block's outer surface 20 to its bone-engaging surface 22. A metallic posterior cutting guide 34 is secured to the posterior cutting surface 30 of the polymer 4-in-1 cutting block 12. The posterior cutting guide 34 is sized and shaped to support and guide the blade (see FIG. 6) of a surgical saw or other cutting instrument and orient the blade to resect the posterior surface of the patient's femur during an orthopaedic surgical procedure. In the illustrative embodiment described herein, the posterior cutting guide 34 is embodied as a non-captured cutting guide, although it may alternatively be embodied as a captured cutting guide.

The 4-in-1 cutting block 12 has a chamfer cutting slot 36 formed near its middle. Specifically, the chamfer cutting slot 36 is located posteriorly of the anterior cutting slot 24 and anteriorly of the posterior cutting surface 30. The chamfer cutting slot 36 is an elongated slot extending in the medial/lateral direction. The chamfer cutting slot 36 extends through the entire thickness of the 4-in-1 cutting block 12—that is, it extends from the cutting block's outer surface 20 to its bone-engaging surface 22 and, as a result, opens to both surfaces. The chamfer cutting slot 36 is defined by a sidewall 38 of the 4-in-1 cutting block that includes an anterior edge 40 extending in the medial/lateral direction and a posterior edge 42 that is spaced apart from the anterior edge 40 and likewise extends in the medial/lateral direction. The chamfer cutting slot 36 has enlarged rounded medial and lateral ends. In particular the medial edge 44 of the sidewall 38 defining the chamfer cutting slot 36 is cylindrical in shape (i.e., circular when viewed in the front elevation of FIG. 2) and has a diameter that is larger than the A/P width of the slot 36 (i.e., the distance between anterior edge 40 and the posterior edge 42 of the sidewall 38). On the opposite end of the chamfer cutting slot 36, the lateral edge 46 of the sidewall 38 is identical in shape and size. In essence, in the illustrative embodiment described herein, the chamber cutting slot 36 takes on the form of two cylinders spaced at opposite medial and lateral ends connected by a elongated planar slot.

Figure 2:
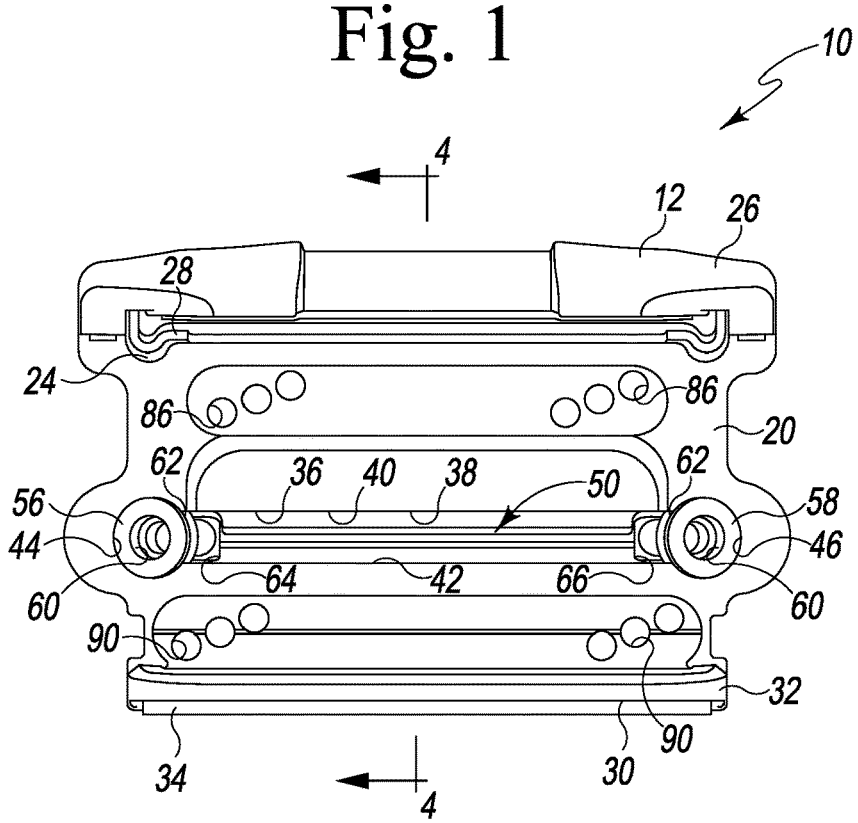
FIG. 2 is an elevation view showing the outer surface of the orthopaedic surgical instrument of FIG. 1.
Figure 3:
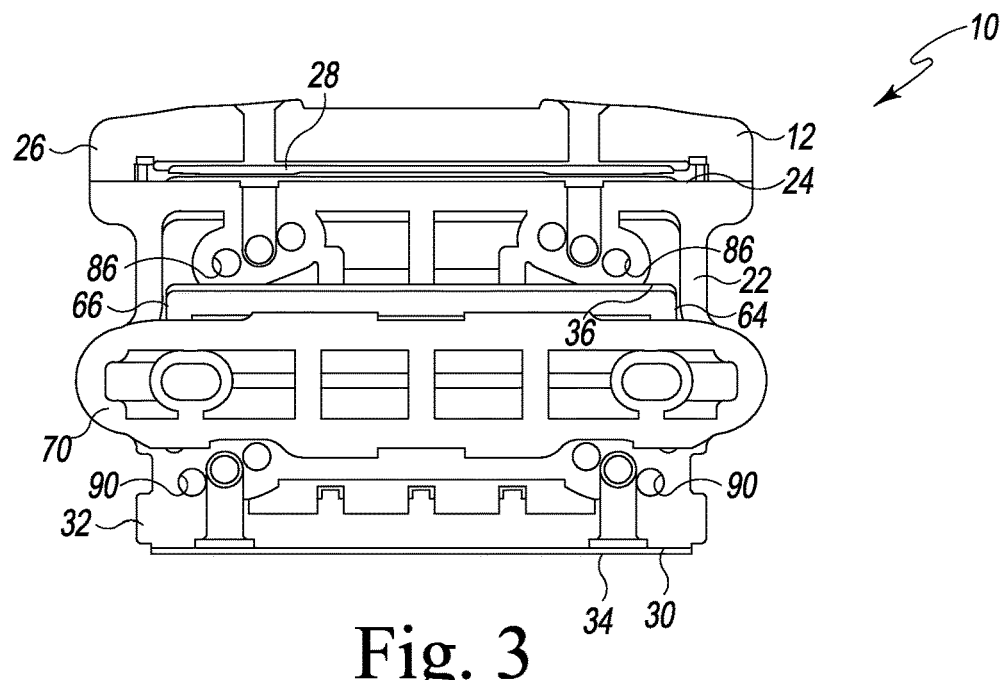
FIG. 3 is an elevation view showing the bone-engaging surface of the orthopaedic surgical instrument of FIG. 1.
Figure 4:
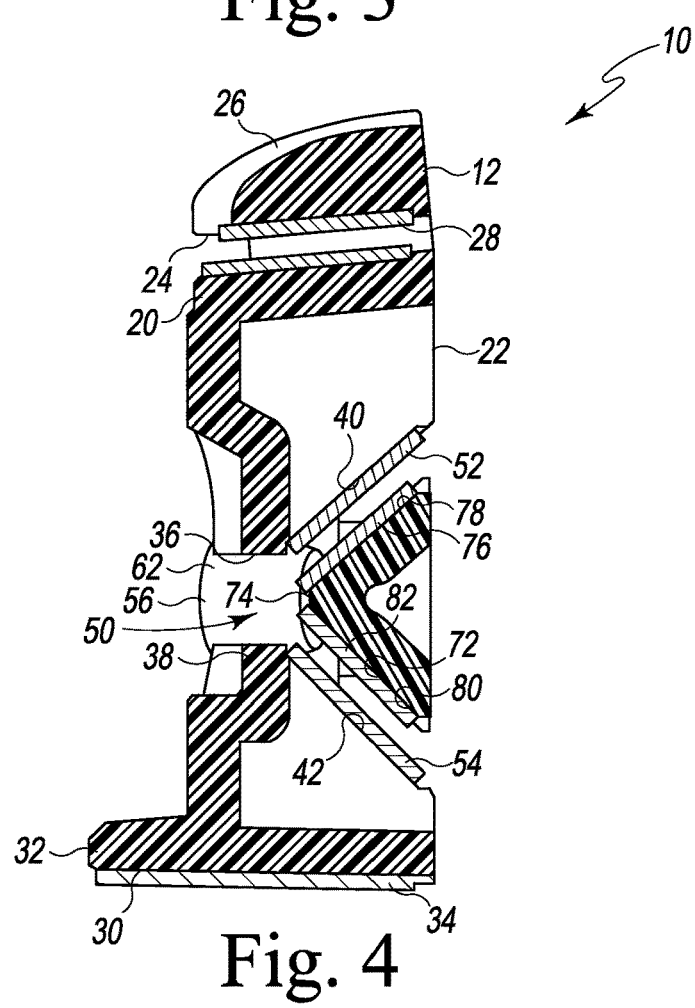
FIG. 4 is a cross section view of the orthopaedic surgical instrument, taken along the line 4-4 of FIG. 2, as viewed in the direction of the arrows.

As can be seen in FIGS. 1, 2, and 4, a metallic captured chamfer cutting guide assembly 50 is positioned in the chamfer cutting slot 36. The chamfer cutting guide assembly 50 includes a metallic planar cutting guide 52 secured to the anterior edge 40 of the sidewall 38 defining the anterior side of the chamfer cutting slot 36, along with a metallic planar cutting guide 54 secured to the posterior edge 42 of the sidewall 38 defining the posterior side of the chamfer cutting slot 36. As can be seen best in FIG. 4, the planar cutting guides 52, 54 are spaced apart from one another in the anterior/posterior direction and are arranged at an oblique angle relative to one another. The longitudinal axis of the planar cutting guides 52, 54 extends in the medial/lateral direction.

The medial and lateral ends of the captured chamfer cutting guide assembly 50 are defined by a pair of metallic bushings 56, 58. In particular, the metallic bushing 56 is positioned in the enlarged cylindrically-shaped medial end of the chamfer cutting slot 36—that is, the metallic bushing 56 is secured in contact with the medial edge 44 of the sidewall 38 defining the medial end of the chamfer cutting slot 36. The metallic bushing 58 is positioned in the enlarged cylindrically-shaped lateral end of the chamfer cutting slot 36—that is, the metallic bushing 58 is secured in contact with the lateral edge 46 of the sidewall 38 defining the lateral end of the chamfer cutting slot 36.

The metallic bushings 56, 58 are cylindrically-shaped and have an elongated bore 60 extending therethrough. The elongated bore 60 is sized to receive a fixation or guide pin for pinning the 4-in-1 cutting block to the patient's distal femur (see FIG. 7), and, optionally, a drill such that the patient's femur may be pre-drilled prior to installation of the guide pins if the surgeon so desires. The metallic bushings 56, 58 are identical in shape and include an annularly-shaped outer surface 62. As can be seen in FIG. 2, the outer surface 62 of the metallic bushing 56 is positioned at the medial end 64 of the planar cutting guides 52, 54, with the outer surface 62 of the metallic bushing 58 being positioned at the lateral end 66 of the planar cutting guides 52, 54. In the illustrative embodiment described herein, the outer surface 62 of the metallic bushings 56, 58 is slightly spaced apart from the respective medial end 64 and lateral end 66 of the planar cutting guides 52, 54 (i.e., the bushings 56, 58 are not positioned in contact with the planar cutting guides 52, 54). Such spacing allows for capture of the blade of a bone saw, while also providing for relief from overly tight tolerances in the manufacturing process. However, in another illustrative embodiment, the metallic bushings 56, 58 are positioned in contact with the respective medial end 64 and lateral end 66 of the planar cutting guides 52, 54.

As can be seen best in FIGS. 1 and 4, the 4-in-1 cutting block 12 has a wedge component 70 secured to its bone-engaging surface 22. Like the 4-in-1 cutting block 12, the wedge component 70 is formed from polymeric materials. The wedge component 70 has a wedge-shaped cutting surface 72. The "leading" edge 74 of the wedge-shaped cutting surface 72 extends into the chamfer cutting slot 36. A metallic planar cutting guide 76 is secured to the anterior surface 78 of the wedge-shaped cutting surface 72, with a metallic planar cutting guide 80 being secured to the posterior surface 82 of the wedge-shaped cutting surface 72. Like the cutting guides 52, 54, the planar cutting guides 76, 80 are spaced apart from one another and are arranged at an oblique angle relative to one another. The longitudinal axis of the planar cutting guides 76, 80 extends in the medial/lateral direction. As can be seen in FIG. 4, the cutting guide 76 is spaced apart from, and parallel to, the cutting guide 52, with the cutting guide 80 being spaced apart from, and parallel to, the cutting guide 54. In such a way, the cutting guides 52, 76 cooperate to guide a saw blade during performance of the anterior chamfer cut, with the cutting guides 54, 80 cooperating to guide the saw blade during performance of the posterior chamfer cut (see FIG. 7).

Like the planar cutting guides 52, 54, the outer surface 62 of the metallic bushing 56 is positioned at the medial end of the planar cutting guides 76, 80, with the outer surface 62 of the metallic bushing 58 being positioned at the lateral end of the planar cutting guides 76, 80. In the illustrative embodiment described herein, the outer surface 62 of the metallic bushings 56, 58 is slightly spaced apart from the respective medial end and lateral end of the planar cutting guides 76, 80 (i.e., the bushings 56, 58 are not positioned in contact with the planar cutting guides 76, 80). Such spacing allows for capture of the blade of a bone saw, while also providing for relief from overly tight tolerances in the manufacturing process. However, in another illustrative embodiment, the metallic bushings 56, 58 are positioned in contact with the respective medial end and lateral end of the planar cutting guides 76, 80.

Figure 6:
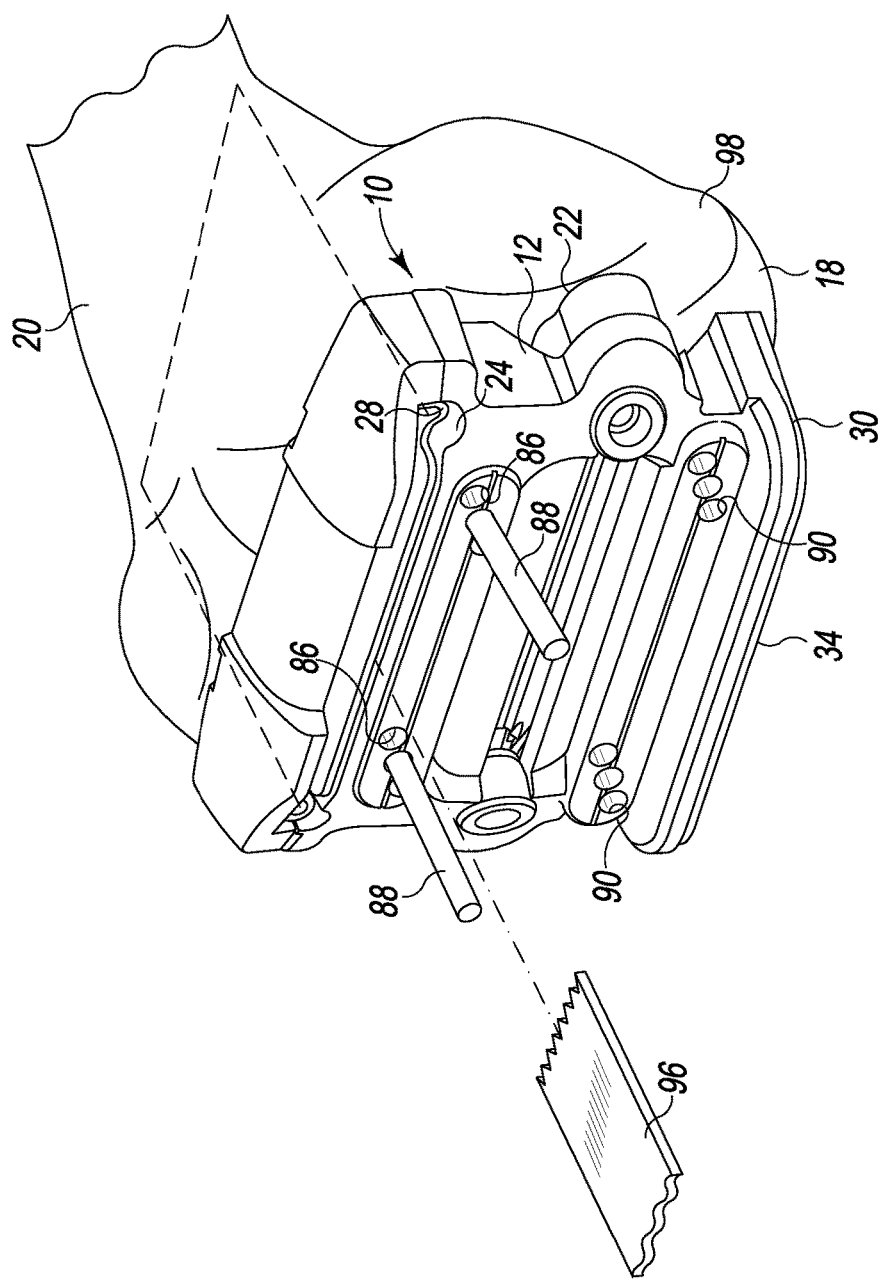
FIG. 6 is a view similar to FIG. 5, but showing the orthopaedic surgical instrument of FIG. 1 being used to perform the anterior and posterior cuts on the distal end of the patient's femur.

The 4-in-1 cutting block 12 has a plurality of guide holes 86 defined therein that are sized to receive a pair of fixation or guide pins 88 (see FIG. 6). The holes 86 are positioned between the anterior cutting slot 24 and the chamfer cutting slot 36 and extend between the outer surface 20 and the bone-engaging surface 22 of the cutting block 12. The holes 86 are arranged in a staggered pattern to permit the surgeon to change the position of the cutting block 12 on the patient's femur without having to remove the fixation pins 88, as described in greater detail below.

The 4-in-1 cutting block 12 also includes another plurality of guide holes 90 positioned between the chamfer cutting 36 and the posterior cutting surface 30. Each guide hole 90 is sized to receive one of the fixation pins 88 in a similar manner to the guide holes 86 and thereby extends between the outer surface 20 and the bone-engaging surface 22 of the cutting block 12. Like the guide holes 86, the guide holes 90 are arranged in a staggered pattern to permit the surgeon to change the position of the cutting block 12 on the patient's femur without having to remove the fixation pins 88.

In operation, the surgeon may utilize the orthopaedic surgical instrument 10 to prepare the distal end 18 of the patient's femur 100 to receive a prosthetic femoral component. To do so, the surgeon may secure the 4-in-1 cutting block 12 to the patient's femur 100 and thereafter use the metallic cutting guides of the cutting block 12 to guide a cutting saw blade in making a series of four resections of the distal end 18 of the patient's femur 100.

Figure 5:
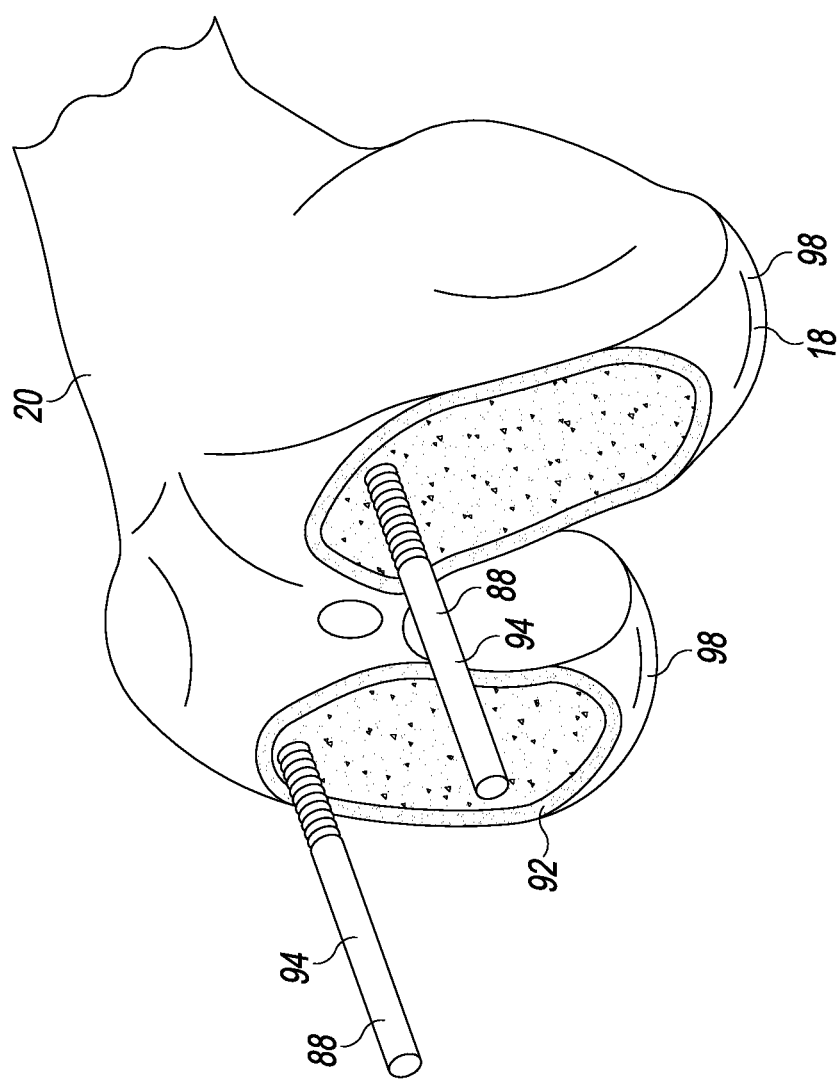
FIG. 5 is a perspective view showing a pair of fixation pins secured to a distal end of a patient's femur.

During an orthopaedic surgical procedure, the surgeon may first resect the distal end 18 of the patient's femur 100 to create a surgically-prepared distal surface 92. The surgeon may then secure a pair of fixation pins 88 to the surgically-prepared distal surface 92 of the patient's femur 100, as shown in FIG. 5. To do so, the surgeon may size the patient's femur 100 for the prosthetic femoral component and set the femoral rotation. One exemplary procedure for locating fixation pins during a femoral sizing and rotation setting procedure is described in the SIGMA® Fixed Reference Surgical Technique by DePuy Orthopaedics, Inc. (2010), which is expressly incorporated herein by reference. After sizing the femoral component and setting the rotation, the surgeon may attach the fixation pins 88 to the surgically-prepared distal surface 92 of the patient's femur 100.

After attaching the fixation pins 88, the surgeon may position the 4-in-1 cutting block 12 on the surgically-prepared distal surface 92 of the patient's femur 100. To do so, the surgeon may align the shafts 94 of the fixation pins 88 with a pair of the guide holes 86 of the 4-in-1 cutting block 12. The surgeon may then advance the 4-in-1 cutting block 12 over the shafts 94 in a direction toward the surgically-prepared distal surface 92 of the patient's femur 100. The bone-engaging surface 22 of the 4-in-1 cutting block 12 contacts the surgically-prepared distal surface 92 when the instrument 10 is positioned on the distal end 18 of the patient's femur 100, as shown in FIG. 6. If the surgeon desires to relocate the 4-in-1 cutting block 12, the surgeon may utilize another combination of guide holes 86 to change the position of the cutting block 12 on the patient's femur 100. If additional fixation is necessary, the surgeon may insert additional fixation pins 88 through the guide holes 90 defined in the 4-in-1 cutting block 12.

Once installed in such a manner, the surgeon may use the 4-in-1 cutting block 12 to make a number of resections of the distal end 18 of the patient's femur 100. For example, as shown in FIG. 6, the anterior cutting guide 28 defines a resection plane that extends through the distal end 18 of the patient's femur 100. The surgeon may advance a cutting tool, such as, for example, a surgical cutting saw 96 through the anterior cutting guide 28 to engage the patient's femur 100 and operate the surgical saw 96 to surgically prepare an anterior surface of the patient's femur 100 to receive the prosthetic femoral component. The surgeon may similarly use the posterior cutting guide 34 to resect the posterior condyles 98 of the patient's femur 100 and surgically prepare the posterior surfaces of the patient's femur 100 to receive the prosthetic femoral component.

Figure 7:
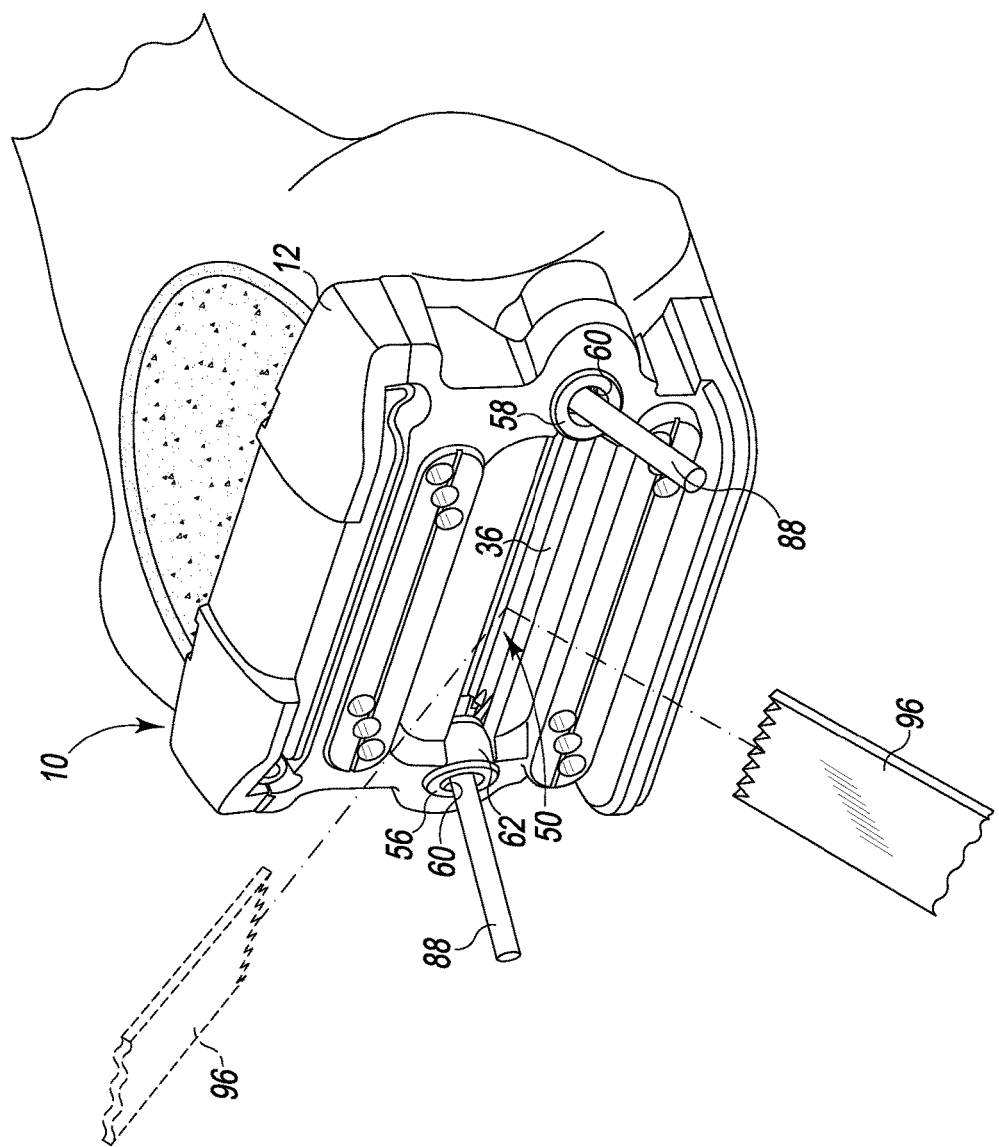
FIG. 7 is a view similar to FIG. 6, but showing the orthopaedic surgical instrument of FIG. 1 being used to perform the chamfer cuts on the distal end of the patient's femur.

As shown in FIG. 7, the surgeon may also use the captured chamfer cutting guide assembly 50 in cooperation with the planar cutting guides 76, 80 of the wedge component 70 to make chamfer cuts on the patient's femur 100. To do so, the surgeon may first insert fixation pins 88 through the elongated bores 60 of the metallic bushings 56, 58 of the chamfer cutting guide assembly 50. The surgeon may then remove any fixation pins 88 from the guide holes 86, 90 since fixation pins 88 positioned in the guide holes 86, 90 would disrupt the chamfer cutting process. The surgeon may then advance the surgical cutting saw 96 through opening between the cutting guides 52, 76 to guide the saw 96 during performance of the anterior chamfer cut (as shown in solid lines in FIG. 7), and thereafter through the opening between the cutting guides 54, 80 to guide the saw 96 during performance of the posterior chamfer cut (as shown in phantom lines in FIG. 7).

During performance of such chamfer cuts, the metallic cutting guides 52, 54 function as a saw stop to prevent the saw 96 from engaging the polymeric body of the 4-in-1 cutting block 12 that defines the anterior and posterior edges of the chamfer cutting slot 36. Similarly, the outer surfaces 62 of the metallic bushings 56, 58 function as a saw stop to prevent the saw from engaging the polymeric body of the of the 4-in-1 cutting block 12 that defines the medial and lateral edges of the chamfer cutting slot 36. Likewise, the wedge component's metallic cutting guides 76, 80 function as a saw stop to prevent the saw 96 from engaging the wedge-shaped cutting surface 72 of the wedge component 70.

Referring now to FIGS. 8-16, other embodiments of 4-in-1 cutting blocks are shown. The embodiments of FIGS. 8-16, like the embodiment of FIGS. 1-7, are single use instruments that may be formed from polymeric materials such as, for example, polyamide, polyphenylsulfone, or polyketone. Like the embodiment of FIGS. 1-7, the surfaces of the embodiments of FIGS. 8-16 used to guide surgical instruments, such as cutting guide surfaces for guiding bone saws and bushings for guiding drills and surgical pins, are formed from a metallic material such as, for example, steel, titanium alloy, or cobalt chromium alloy. Such use of metallic components or "inserts" prevents the surgical tools from coming into contact with the polymeric materials of the block's body.

Figure 8:
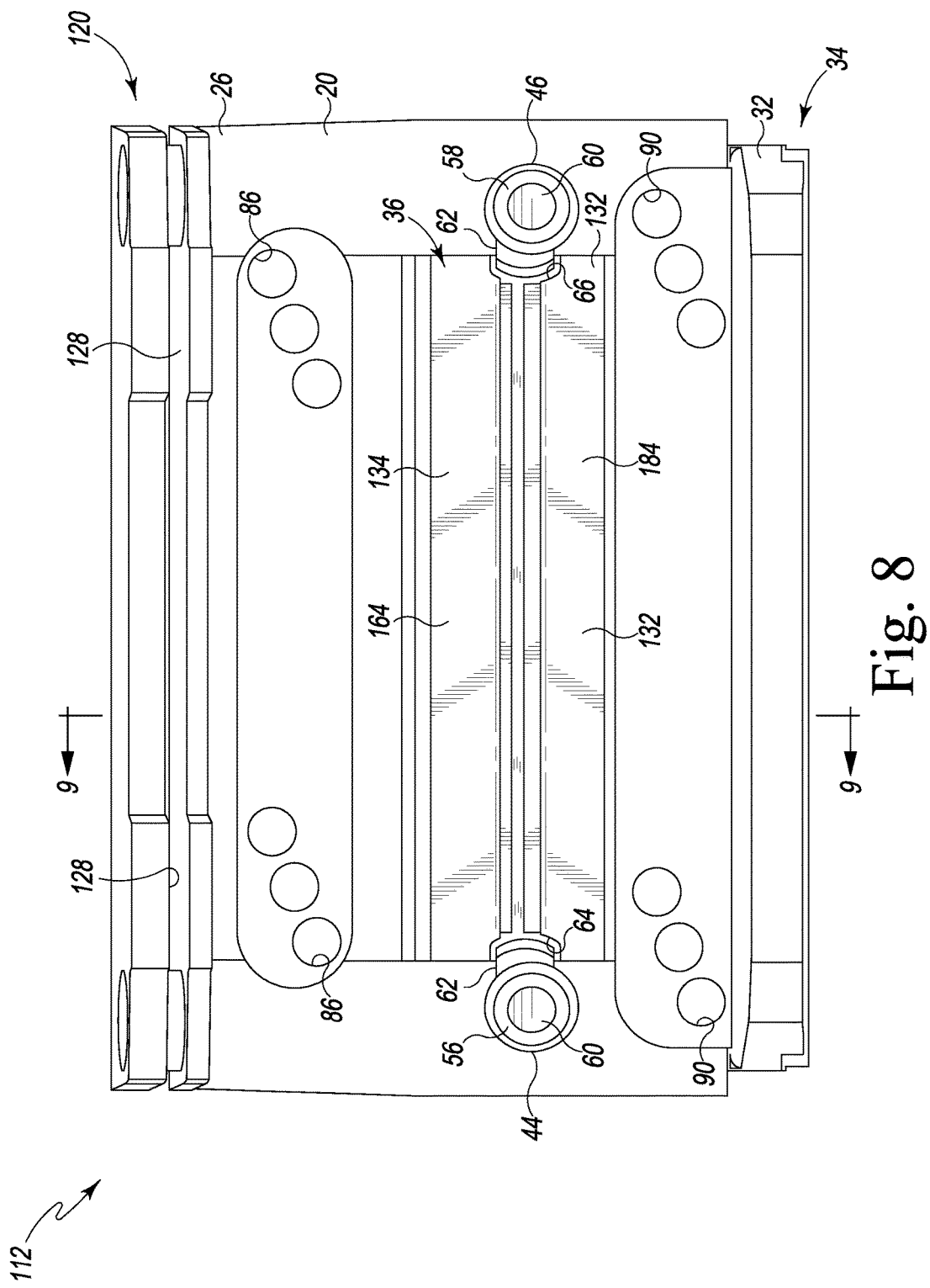
FIG. 8 is a front elevation view of another embodiment of an orthopaedic surgical instrument.
Figure 9:
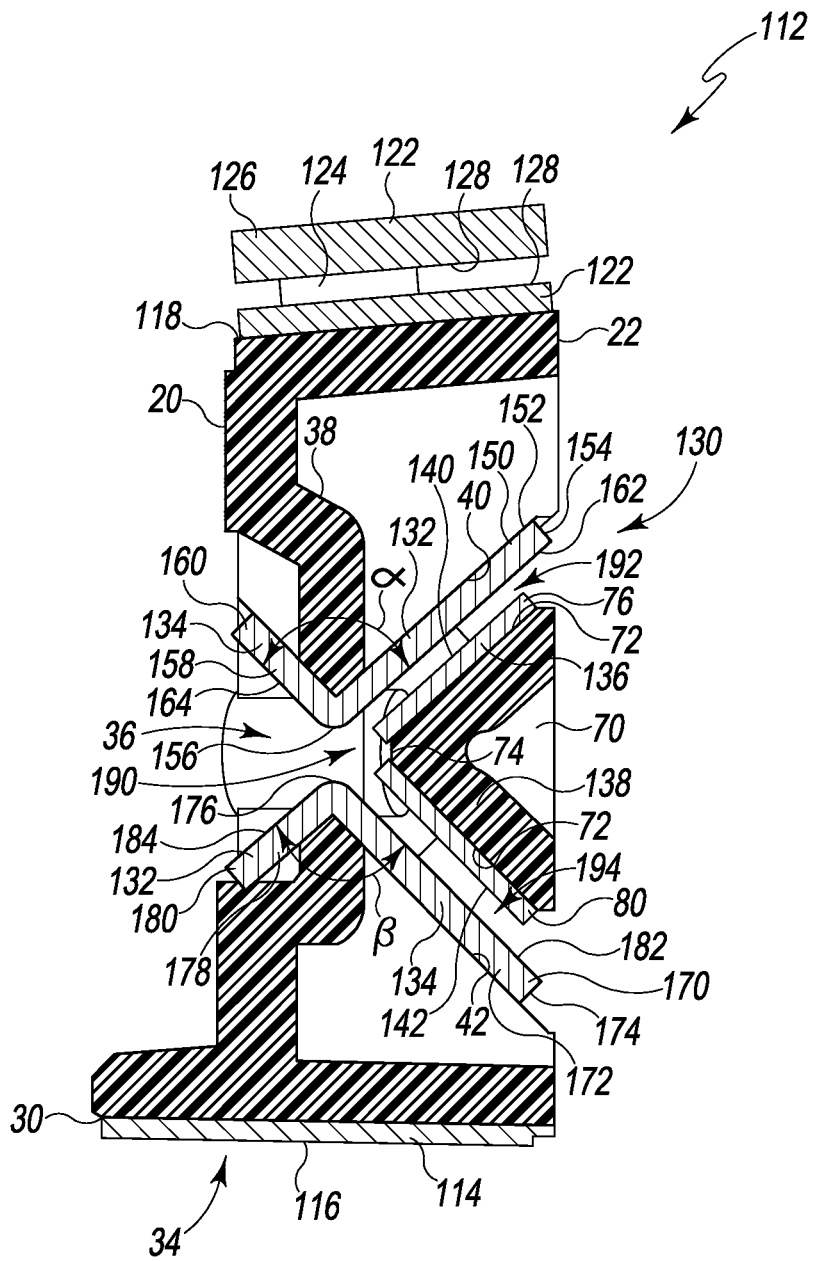
FIG. 9 is a cross section view of the orthopaedic surgical instrument, taken along the line 9-9 in FIG. 8, as viewed in the direction of the arrows.

The embodiment of FIGS. 8-9 includes features similar to those discussed above in regard to the embodiment of FIGS. 1-7. Those features are identified in FIGS. 8-9 with the same reference numbers used in FIGS. 1-7. For example, as shown in FIGS. 8-9, the 4-in-1 cutting block (hereinafter 4-in-1 cutting block 112) includes an outer surface 20 and a bone-engaging surface 22 positioned opposite the outer surface 20. The 4-in-1 cutting block 112 also has a posterior cutting surface 30 formed near its posterior end 32 and a metallic posterior cutting guide 34 secured to the surface 30. As shown in FIG. 9, the metallic posterior cutting guide 34 includes a metallic plate 114 that extends in the medial/lateral direction. The metallic plate 114 includes a planar surface 116 that guides the blade 96 of the surgical saw during the orthopaedic surgical procedure.

The 4-in-1 cutting block 112 has an anterior cutting surface 118 formed near its anterior end 26. The anterior cutting surface 118 is an elongated surface extending in the medial/lateral direction. The anterior cutting surface 118 extends through the entire thickness of the 4-in-1 cutting block 112—that is, the anterior cutting surface 118 extends from the cutting block's outer surface 20 to its bone-engaging surface 22. A metallic anterior cutting guide assembly 120 is secured to the anterior cutting surface 118 of the polymer 4-in-1 cutting block 112. The anterior cutting guide assembly 120 is embodied as a captured cutting guide, although the cutting guide assembly 120 may alternatively be embodied as a non-captured cutting guide. The anterior cutting guide assembly 120 is sized and shaped to receive the blade 96 of the surgical saw or other cutting instrument and orient the blade to resect the anterior surface of the patient's femur during an orthopaedic surgical procedure.

As shown in FIG. 9, the metallic anterior cutting guide assembly 120 includes a pair of opposing metallic anterior cutting guides 122 secured to the anterior cutting guide surface 118. The metallic anterior cutting guides 122 are connected to, and spaced apart from, each other by a pair of posts 124 positioned near the longitudinal ends of the assembly 120. Each guide 122 includes a metallic plate 126 that extends in the medial/lateral direction. The metallic plates 126 include opposing planar surfaces 128 that cooperate to guide the blade 96 of the surgical saw during the orthopaedic surgical procedure.

The 4-in-1 cutting block 112 has a chamfer cutting slot 36 formed near its middle. Specifically, the chamfer cutting slot 36 is located posteriorly of the anterior cutting surface 118 and anteriorly of the posterior cutting surface 30. The chamfer cutting slot 36 is an elongated slot extending in the medial/lateral direction. The chamfer cutting slot 36 extends through the entire thickness of the 4-in-1 cutting block 112—that is, it extends from the cutting block's outer surface 20 to its bone-engaging surface 22 and, as a result, opens to both surfaces. The chamfer cutting slot 36 is defined by a sidewall 38 of the 4-in-1 cutting block that includes an anterior edge 40 extending in the medial/lateral direction and a posterior edge 42 that is spaced apart from the anterior edge 40 and likewise extends in the medial/lateral direction.

As shown in FIG. 9, a metallic chamfer cutting guide assembly 130 is positioned in the chamfer cutting slot 36. The chamfer cutting guide assembly 130 includes a metallic planar cutting guide 132 and a metallic planar cutting guide 134, which are arranged at an oblique angle relative to one another. The longitudinal axis of the planar cutting guides 132, 134 extends in the medial/lateral direction. The chamfer cutting guide assembly 130 also includes a metallic planar cutting guide 76 and a metallic planar cutting guide 80, which are spaced apart from one another and are arranged at an oblique angle relative to one another. The longitudinal axis of the planar cutting guides 76, 80 extends in the medial/lateral direction.

Like the embodiment of FIGS. 1-7, the 4-in-1 cutting block 112 has a wedge component 70 secured to its bone-engaging surface 22. The wedge component 70 is formed from polymeric materials and has a wedge-shaped cutting surface 72. The "leading" edge 74 of the wedge-shaped cutting surface 72 extends into the chamfer cutting slot 36. The metallic planar cutting guide 76 includes a metallic plate 136 that is secured to the anterior surface 78 of the wedge-shaped cutting surface 72. The metallic planar cutting guide 80 includes a metallic plate 138 that is secured to the posterior surface 82 of the wedge-shaped cutting surface 72. The metallic plates 136, 138 include planar surface 140, 142, respectively, that are arranged at an oblique angle relative to one another.

The chamfer cutting guide assembly 130 also includes a metallic body 150 that is secured to the anterior edge 40 of the sidewall 38 that defines the anterior side of the chamfer cutting slot 36. The body 150 includes a plate 152 that extends from an end 154 positioned adjacent to the bone-engaging surface 22 to an inner end 156. Another plate 158 extends from the inner end 156 to an end 160 positioned adjacent to the cutting block's outer surface 20. The plates 152, 158 have planar surfaces 162, 164, respectively, that are connected at the inner end 156. As shown in FIG. 9, an angle α is defined between the planar surfaces 162, 164. In the illustrative embodiment, the angle α is an oblique angle and may have a magnitude in a range of, for example, 45 degrees to 135 degrees.

As described above, the 4-in-1 cutting guide 112 includes a posterior edge 42 that defines the posterior side of the chamfer cutting slot 36. Another metallic body 170 is secured to the posterior edge 42, and the body 170 includes a plate 172 that extends from an end 174 positioned adjacent to the bone-engaging surface 22 to an inner end 176. Another plate 178 extends from the inner end 176 to an end 180 positioned adjacent to the cutting block's outer surface 20. The plates 172, 178 have planar surfaces 182, 184, respectively, that are connected at the inner end 176. As shown in FIG. 9, an angle β is defined between the planar surfaces 182, 184. In the illustrative embodiment, the angle β is an oblique angle and may have a magnitude in a range of, for example, 45 degrees to 135 degrees.

As shown in FIG. 9, the inner end 156 of the metallic body 150 defines an apex. The inner end 176 of the metallic body 170 is positioned opposite the inner end 156 and defines an apex of the metallic body 170. An opening 190 sized to receive the saw blade 96 is defined between the inner ends 156, 176 of the bodies 150, 170.

In the illustrative embodiment, the metallic planar cutting guide 132 of the chamfer cutting guide assembly 130 is defined by the plate 152 of the body 150 and the plate 178 of the body 170. As shown in FIG. 9, the end 154 of the body 150 defines the anterior end of the metallic planar cutting guide 132 and the end 180 of the body 170 defines the posterior end of the metallic planar cutting guide 132. The plates 152, 178 (and hence the planar surfaces 162, 184) of the metallic planar cutting guide 132 and the plate 136 (and hence surface 140) of the metallic planar cutting guide 76 are spaced apart, and extend parallel to, each other. A passageway 192 sized to receive the saw blade 96 is defined between the plates 136, 152, and the plates 136, 152, 178 cooperate to guide the saw blade 96 during the performance of an anterior chamfer cut.

As described above, the chamfer cutting guide assembly 130 also includes a metallic planar cutting guide 134 that extends at an oblique angle relative to the metallic planar cutting guide 132. The metallic planar cutting guide 134 is defined by the plate 158 of the body 150 and the plate 172 of the body 170. As shown in FIG. 9, the end 160 of the body 150 defines the anterior end of the metallic planar cutting guide 134 and the end 174 of the body 170 defines the posterior end of the metallic planar cutting guide 134. The plates 158, 172 (and hence the planar surfaces 164, 182) of the metallic planar cutting guide 134 and the plate 138 (and hence surface 142) of the metallic planar cutting guide 80 are spaced apart, and extend parallel to, each other. A passageway 194 sized to receive the saw blade 96 is defined between the plates 138, 172, and the plates 138, 158, 172 cooperate to guide the saw blade 96 during the performance of a posterior chamfer cut.

Like the embodiment of FIGS. 1-7, the medial and lateral ends of the chamfer cutting guide assembly 130 are defined by a pair of metallic bushings 56, 58. In particular, the metallic bushing 56 is positioned in an enlarged cylindrically-shaped medial end of the chamfer cutting slot 36—that is, the metallic bushing 56 is secured in contact with the medial edge 44 of the sidewall 38 defining the medial end of the chamfer cutting slot 36. The metallic bushing 58 is positioned in an enlarged cylindrically-shaped lateral end of the chamfer cutting slot 36—that is, the metallic bushing 58 is secured in contact with the lateral edge 46 of the sidewall 38 defining the lateral end of the chamfer cutting slot 36.

The metallic bushings 56, 58 are cylindrically-shaped and have an elongated bore 60 extending therethrough. The elongated bore 60 is sized to receive a fixation or guide pin for pinning the 4-in-1 cutting block to the patient's distal femur, and, optionally, a drill such that the patient's femur may be pre-drilled prior to installation of the guide pins if the surgeon so desires. The metallic bushings 56, 58 are identical in shape and include an annularly-shaped outer surface 62. As can be seen in FIG. 8, the outer surface 62 of the metallic bushing 56 is positioned at the medial end 64 of the planar cutting guides 132, 134, with the outer surface 62 of the metallic bushing 58 being positioned at the lateral end 66 of the planar cutting guides 132, 134. In the illustrative embodiment described herein, the outer surface 62 of the metallic bushings 56, 58 is slightly spaced apart from the respective medial end 64 and lateral end 66 of the planar cutting guides 132, 134 (i.e., the bushings 56, 58 are not positioned in contact with the planar cutting guides 132, 134). Such spacing allows for capture of the blade of a bone saw, while also providing for relief from overly tight tolerances in the manufacturing process. However, in another illustrative embodiment, the metallic bushings 56, 58 are positioned in contact with the respective medial end 64 and lateral end 66 of the planar cutting guides 132, 134.

Like the planar cutting guides 132, 134, the outer surface 62 of the metallic bushing 56 is positioned at the medial end of the planar cutting guides 76, 80, with the outer surface 62 of the metallic bushing 58 being positioned at the lateral end of the planar cutting guides 76, 80. In the illustrative embodiment described herein, the outer surface 62 of the metallic bushings 56, 58 is slightly spaced apart from the respective medial end and lateral end of the planar cutting guides 76, 80 (i.e., the bushings 56, 58 are not positioned in contact with the planar cutting guides 76, 80). Such spacing allows for capture of the blade of a bone saw, while also providing for relief from overly tight tolerances in the manufacturing process. However, in another illustrative embodiment, the metallic bushings 56, 58 may be positioned in contact with the respective medial end and lateral end of the planar cutting guides 76, 80.

The 4-in-1 cutting block 112 has a plurality of guide holes 86 defined therein that are sized to receive a pair of fixation or guide pins 88 (see FIG. 6). The holes 86 are positioned between the anterior cutting slot 24 and the chamfer cutting slot 36 and extend between the outer surface 20 and the bone-engaging surface 22 of the cutting block 112. The 4-in-1 cutting block 112 also includes another plurality of guide holes 90 positioned between the chamfer cutting 36 and the posterior cutting surface 30. Each guide hole 90 is sized to receive one of the fixation pins 88 in a similar manner to the guide holes 86 and thereby extends between the outer surface 20 and the bone-engaging surface 22 of the cutting block 112.

In operation, the surgeon may attach the cutting block 112 to the patient's femur 100 in a manner similar to that described above in regard to the cutting block 12. Once attached, the surgeon may also use the planar cutting guides 76, 80, 132, 134 to make chamfer cuts on the patient's femur 100. To do so, the surgeon may first insert fixation pins 88 through the elongated bores 60 of the metallic bushings 56, 58 of the chamfer cutting guide assembly 130. The surgeon may remove any fixation pins 88 from the guide holes 86, 90 since fixation pins 88 positioned in the guide holes 86, 90 would disrupt the chamfer cutting process.

The surgeon may then advance the surgical cutting saw 96 through the opening 190 defined between the metallic bodies 150, 170 and into the passageway 192 defined between the cutting guides 76, 132 to guide the saw blade 96 during the performance of the anterior chamfer cut. As the saw blade 96 makes the cut, the saw blade 96 engages the surfaces 140, 162, 184 of the cutting guides 76, 132. It should be appreciated that the addition of the surface 184 in the chamfer cutting guide assembly 130 provides the saw blade 96 with a longer contact area than is present in the chamfer cutting guide assembly 50 described above in regard to FIGS. 1-7.

The surgeon may advance the surgical cutting saw 96 through the opening 190 defined between the metallic bodies 150, 170 and into the passageway 194 defined between the cutting guides 76, 134 to guide the saw blade 96 during the performance of the posterior chamfer cut. As the saw blade 96 makes the cut, the saw blade 96 engages the surfaces 142, 164, 182 of the cutting guides 76, 134. It should be appreciated that the addition of the surface 164 in the chamfer cutting guide assembly 130 provides the saw blade 96 with a longer contact area than is present in the chamfer cutting guide assembly 50 described above in regard to FIGS. 1-7.

During performance of such chamfer cuts, the metallic cutting guides 132, 134 function as a saw stop to prevent the saw blade 96 from engaging the polymeric body of the 4-in-1 cutting block 112 that defines the anterior and posterior edges of the chamfer cutting slot 36. Similarly, the outer surfaces 62 of the metallic bushings 56, 58 function as a saw stop to prevent the saw from engaging the polymeric body of the of the 4-in-1 cutting block 112 that defines the medial and lateral edges of the chamfer cutting slot 36. Likewise, the wedge component's metallic cutting guides 76, 80 function as a saw stop to prevent the saw 96 from engaging the wedge-shaped cutting surface 72 of the wedge component 70.

Figure 10:
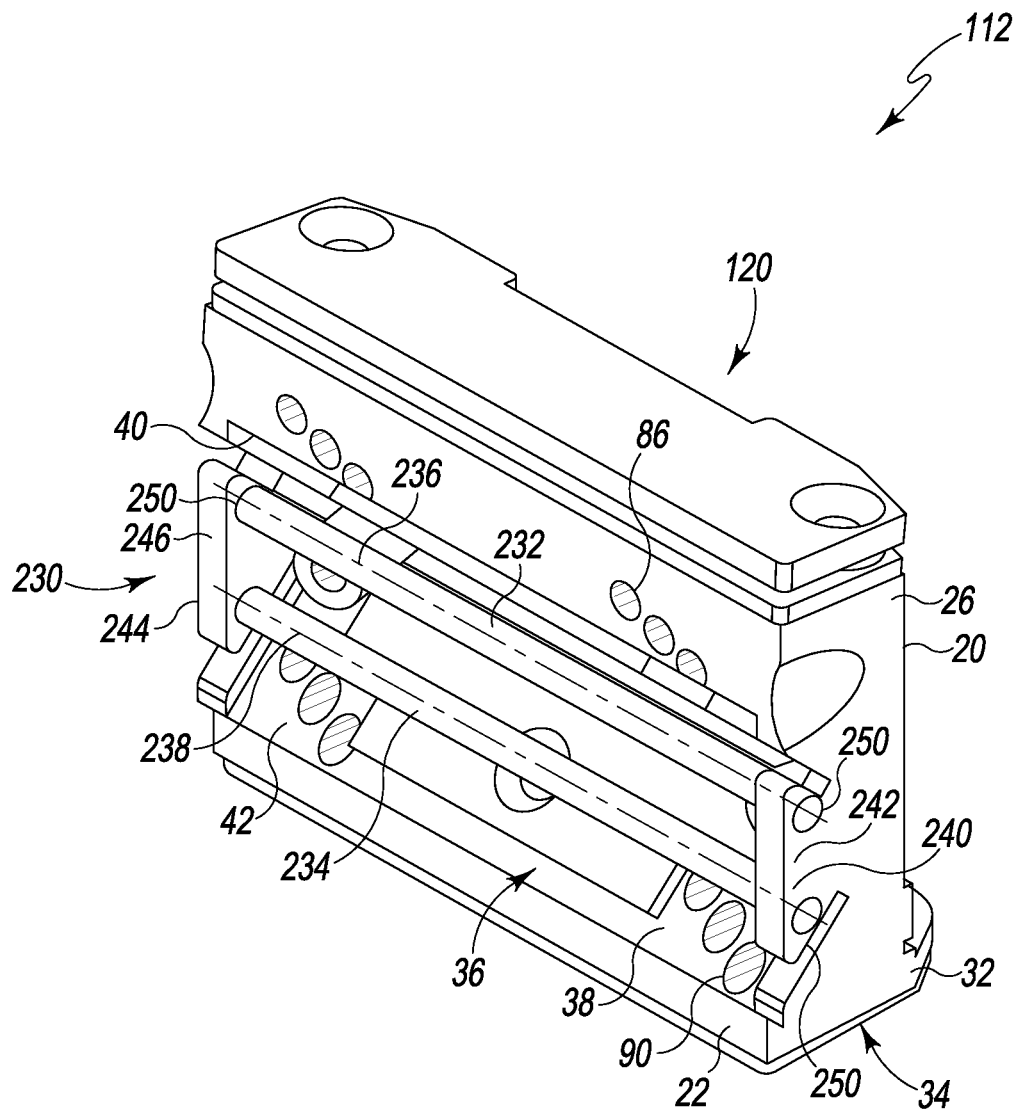
FIG. 10 is a rear perspective of another embodiment of an orthopaedic surgical instrument.
Figure 11:
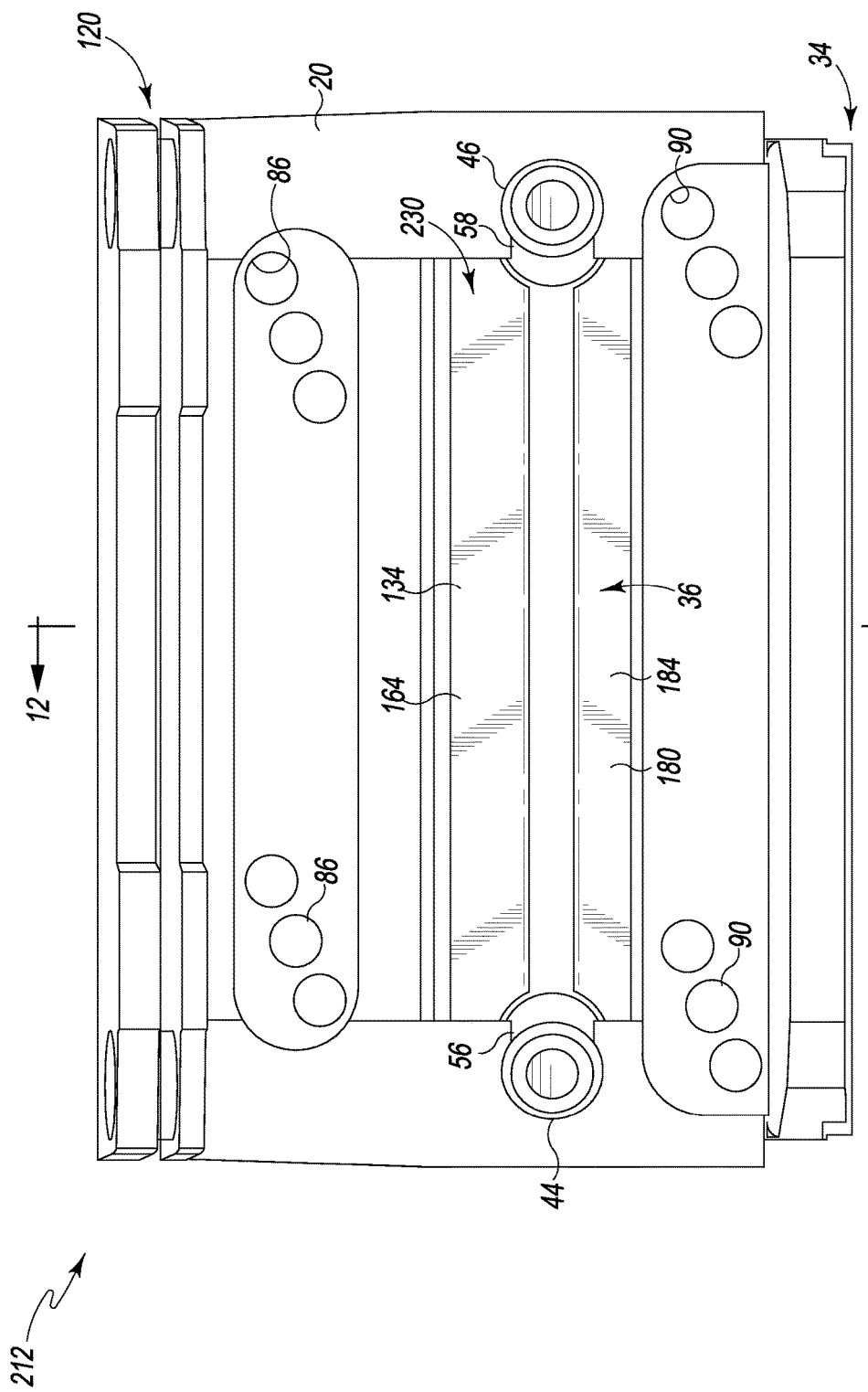
FIG. 11 is a front elevation view of the orthopaedic surgical instrument of FIG. 10.
Figure 12:
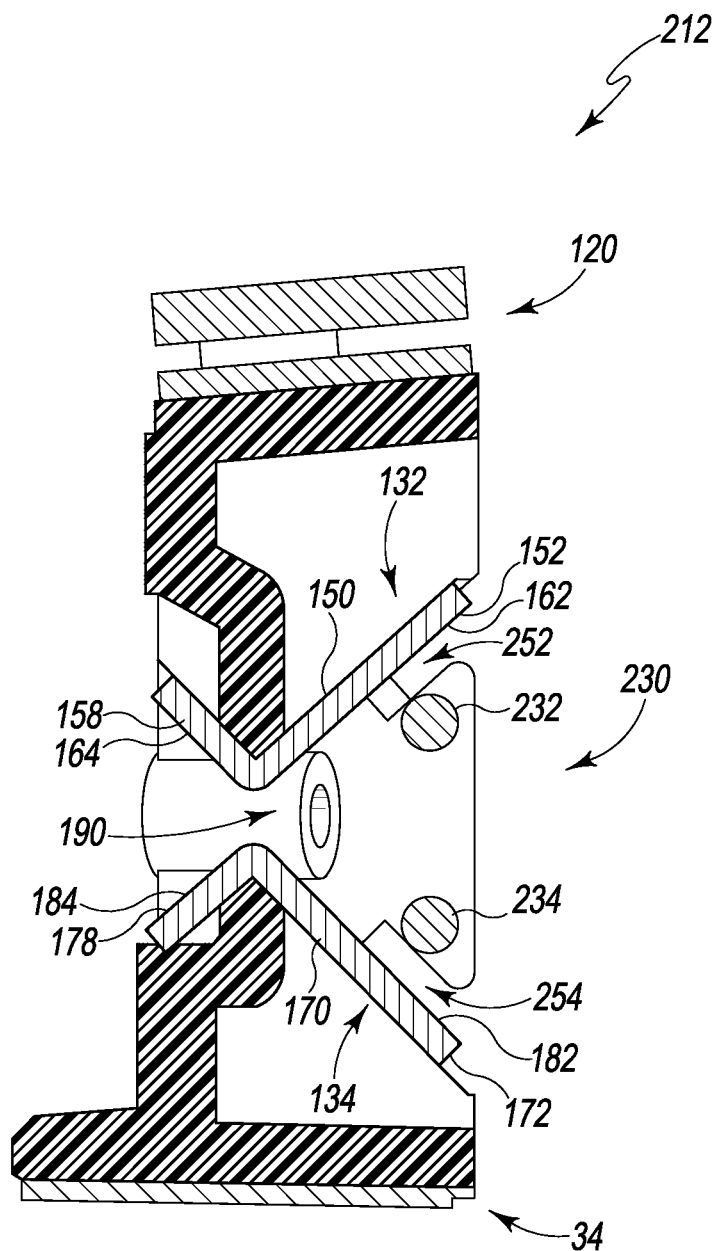
FIG. 12 is a cross section view of the orthopaedic surgical instrument, taken along the line 12-12 in FIG. 11, as viewed in the direction of the arrows.
Figure 13:
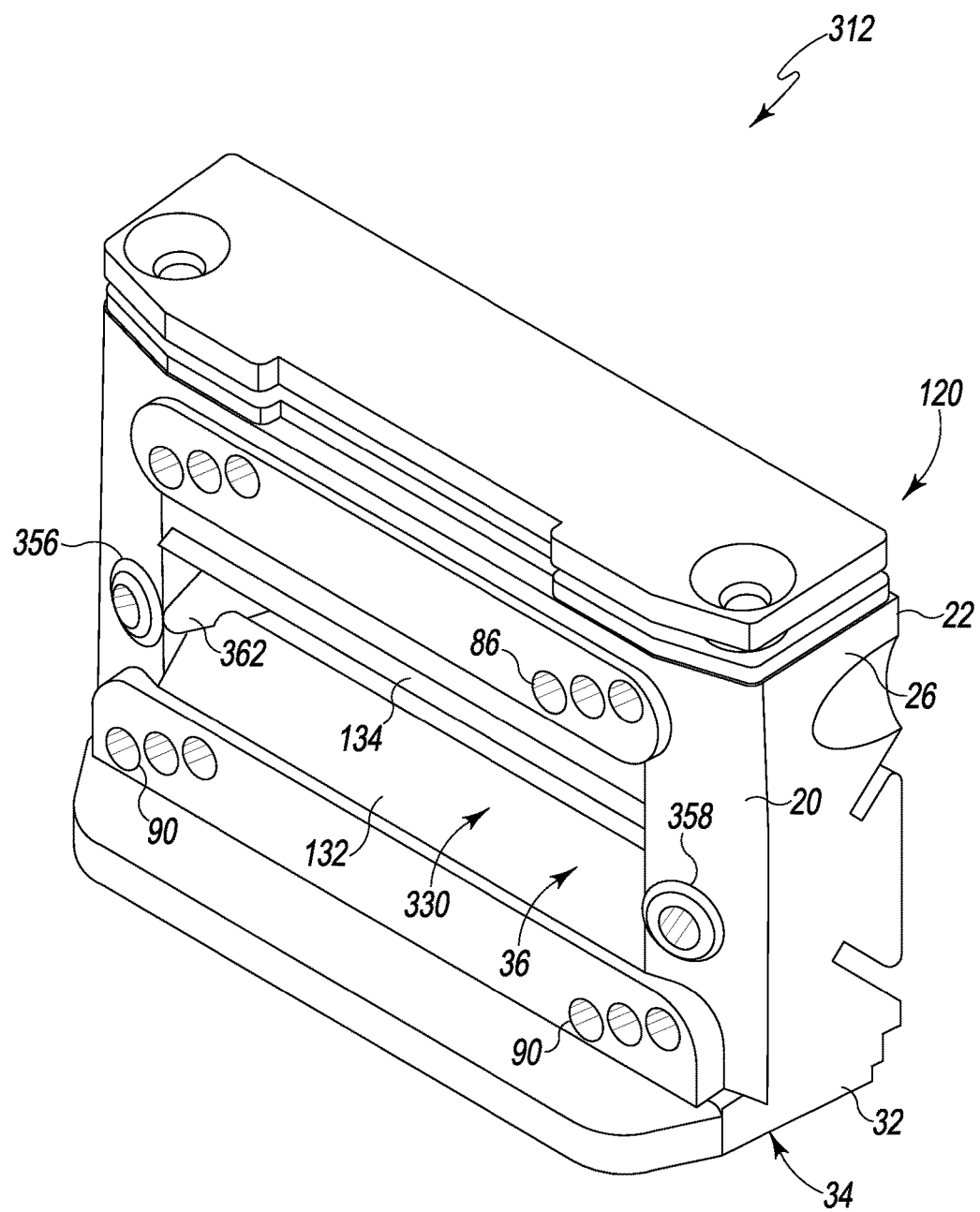
FIG. 13 is a front perspective of another embodiment of an orthopaedic surgical instrument.

Referring now to FIGS. 10-12, another embodiment of a 4-in-1 cutting block (hereinafter cutting block 212) is shown. The embodiment of FIGS. 10-12 includes features similar to those discussed above in regard to the embodiments of FIGS. 1-9. Those features are identified in FIGS. 10-12 with the same reference numbers used in FIGS. 1-9. For example, as shown in FIGS. 10-12, the cutting block 212 includes an outer surface 20 and a bone-engaging surface 22 positioned opposite the outer surface 20. The 4-in-1 cutting block 212 also has a posterior cutting surface 30 formed near its posterior end 32 and a metallic posterior cutting guide 34 secured to the surface 30. An anterior cutting surface 118 is formed near the cutting block's anterior end 26, and a metallic anterior cutting guide assembly 120 is secured to the anterior cutting surface 118.

The 4-in-1 cutting block 212 has a chamfer cutting slot 36 formed near its middle. Specifically, the chamfer cutting slot 36 is located posteriorly of the anterior cutting surface 118 and anteriorly of the posterior cutting surface 30. The chamfer cutting slot 36 is an elongated slot extending in the medial/lateral direction. The chamfer cutting slot 36 extends through the entire thickness of the 4-in-1 cutting block 212—that is, it extends from the cutting block's outer surface 20 to its bone-engaging surface 22 and, as a result, opens to both surfaces. The chamfer cutting slot 36 is defined by a sidewall 38 of the 4-in-1 cutting block that includes an anterior edge 40 extending in the medial/lateral direction and a posterior edge 42 that is spaced apart from the anterior edge 40 and likewise extends in the medial/lateral direction.

A metallic chamfer cutting guide assembly 230 is positioned in the chamfer cutting slot 36 of the cutting block 212. The chamfer cutting guide assembly 230 includes a metallic planar cutting guide 132 and a metallic planar cutting guide 134 that are arranged at an oblique angle relative to one another. The chamfer cutting guide assembly 230 also includes a pair of guide rods 232, 234, which are spaced apart from one another and are positioned adjacent to the bone-engaging surface 22. The longitudinal axes 236, 238 of the guide rods 232, 234, respectively, extend in the medial/lateral direction.

As shown in FIG. 10, a wedge component 240 is secured at the medial end 242 of the cutting block 212. Another wedge component 244 is secured at the lateral end 246 of the cutting block 212. Each of the rods 232, 234 is illustratively embodied as a metal cylinder extending between the components 240, 244. The longitudinal ends of the rods 232, 234 are received in corresponding holes 250 defined in the components 240, 244. While the rods 232, 234 illustratively include cylindrical outer surfaces, it should be appreciated that in other embodiments the rods 232, 234 may have planar or flat surfaces.

As shown in FIG. 12, the metallic planar cutting guide 132 of the chamfer cutting guide assembly 230 is defined by a plate 152 of a metallic body 150 and a plate 178 of a metallic body 170. The plates 152, 178 (and hence the planar surfaces 162, 184) of the metallic planar cutting guide 132 are spaced apart, and extend parallel to, each other. Additionally, the guide rod 232 is spaced apart from the plate 152 such that a through slot 252 is defined between the plate 152 and the rod 232. In that way, the plates 152, 178 cooperate with the rod 232 to guide the saw blade 96 during the performance of an anterior chamfer cut.

The other metallic planar cutting guide 134 of the chamfer cutting guide assembly 230 is defined by a plate 158 of a metallic body 150 and a plate 172 of a metallic body 170. The plates 158, 172 (and hence the planar surfaces 164, 182) of the metallic planar cutting guide 134 are spaced apart, and extend parallel to, each other. Additionally, the guide rod 234 is spaced apart from the plate 172 such that a through slot 254 is defined between the plate 172 and the rod 234. In that way, the plates 158, 172 cooperate with the rod 234 to guide the saw blade 96 during the performance of a posterior chamfer cut.

Like the embodiments of FIGS. 1-9, the medial and lateral ends of the chamfer cutting guide assembly 230 are defined by a pair of metallic bushings 56, 58. The 4-in-1 cutting block 212 also has a plurality of guide holes 86 defined therein that are sized to receive a pair of fixation or guide pins 88. The 4-in-1 cutting block 212 also includes another plurality of guide holes 90 that are sized to receive one of the fixation pins in a similar manner to the guide holes 86 and thereby extends between the outer surface 20 and the bone-engaging surface 22 of the cutting block 212.

In operation, the surgeon may attach the cutting block 212 to the patient's femur 100 in a manner similar to that described above in regard to the cutting blocks 12, 112. Once attached, the surgeon may also use the planar cutting guides 132, 134 and the cutting guide rods 232, 234 to make chamfer cuts on the patient's femur 100. To do so, the surgeon may insert fixation pins 88 through the elongated bores 60 of the metallic bushings 56, 58 of the chamfer cutting guides assembly 50. The surgeon may remove any fixation pins 88 from the guide holes 86, 90 since fixation pins 88 positioned in the guide holes 86, 90 would disrupt the chamfer cutting process.

The surgeon may advance the surgical cutting saw blade 96 through the opening 190 defined between the metallic bodies 150, 170. The blade 96 may be advanced into the slot 254 defined between the cutting guide 132 and the guide rod 232 to guide the saw blade 96 during the performance of the anterior chamfer cut. As the saw blade 96 makes the cut, the saw blade 96 engages the surfaces 162, 184 of the cutting guide 132 and the cylindrical outer surface of the guide rod 232.

The surgeon may advance the surgical cutting saw blade 96 through the opening 190 defined between the metallic bodies 150, 170. The blade 96 may be advanced into the slot 254 defined between the cutting guide 134 and the guide rod 234 to guide the saw blade 96 during the performance of the posterior chamfer cut. As the saw blade 96 makes the cut, the saw blade 96 engages the surfaces 164, 182 of the cutting guide 134 and the outer cylindrical surface of the guide rod 234.

Referring now to FIGS. 13-16, another embodiment of a 4-in-1 cutting block (hereinafter cutting block 312) is shown. The embodiment of FIGS. 13-16 includes features similar to those discussed above in regard to the embodiments of FIGS. 1-12. Those features are identified in FIGS. 13-16 with the same reference numbers used in FIGS. 1-12. For example, as shown in FIGS. 13-16, the cutting block 312 includes an outer surface 20 and a bone-engaging surface 22 positioned opposite the outer surface 20. The 4-in-1 cutting block 412 also has a posterior cutting surface 30 formed near its posterior end 32 and a metallic posterior cutting guide 34 secured to the surface 30. An anterior cutting surface 118 is formed near the cutting block's anterior end 26, and a metallic anterior cutting guide assembly 120 is secured to the anterior cutting surface 118.

The 4-in-1 cutting block 312 has a chamfer cutting slot 36 formed near its middle. Specifically, the chamfer cutting slot 36 is located posteriorly of the anterior cutting surface 118 and anteriorly of the posterior cutting surface 30. The chamfer cutting slot 36 is an elongated slot extending in the medial/lateral direction. The chamfer cutting slot 36 extends through the entire thickness of the 4-in-1 cutting block 312—that is, it extends from the cutting block's outer surface 20 to its bone-engaging surface 22 and, as a result, opens to both surfaces. The chamfer cutting slot 36 is defined by a sidewall 38 of the 4-in-1 cutting block that includes an anterior edge 40 extending in the medial/lateral direction and a posterior edge 42 that is spaced apart from the anterior edge 40 and likewise extends in the medial/lateral direction.

A metallic chamfer cutting guide assembly 330 is positioned in the chamfer cutting slot 36 of the cutting block 312. The chamfer cutting guide assembly 130 includes a metallic planar cutting guide 132 and a metallic planar cutting guide 134, which are arranged at an oblique angle relative to one another. Similar to the embodiments described above, the chamfer cutting guide assembly 330 includes a metallic body 150 that is secured to the anterior edge 40 of the sidewall 38 defining the anterior side of the chamfer cutting slot 36. The body 150 includes a plate 152 that extends from an end 154 positioned adjacent to the bone-engaging surface 22 to an inner end 156. Another plate 158 extends from the inner end 156 to an end 160 positioned adjacent to the cutting block's outer surface 20. The plates 152, 158 have planar surfaces 162, 164, respectively, that are connected at the inner end 156. An angle α is defined between the planar surfaces 162, 164. In the illustrative embodiment, the angle α is an oblique angle and may have a magnitude in a range of, for example, 45 degrees to 135 degrees.

Another metallic body 170 is secured to the posterior edge 42 of the sidewall 38 that defines the posterior side of the chamfer cutting slot 36. The body 170 includes a plate 172 that extends from an end 174 positioned adjacent to the bone-engaging surface 22 to an inner end 176. Another plate 178 extends from the inner end 176 to an end 180 positioned adjacent to the cutting block's outer surface 20. The plates 172, 178 have planar surfaces 182, 184, respectively, that are connected at the inner end 176. An angle β is defined between the planar surfaces 182, 184. In the illustrative embodiment, the angle β is an oblique angle and may have a magnitude in a range of, for example, 45 degrees to 135 degrees.

Figure 16:
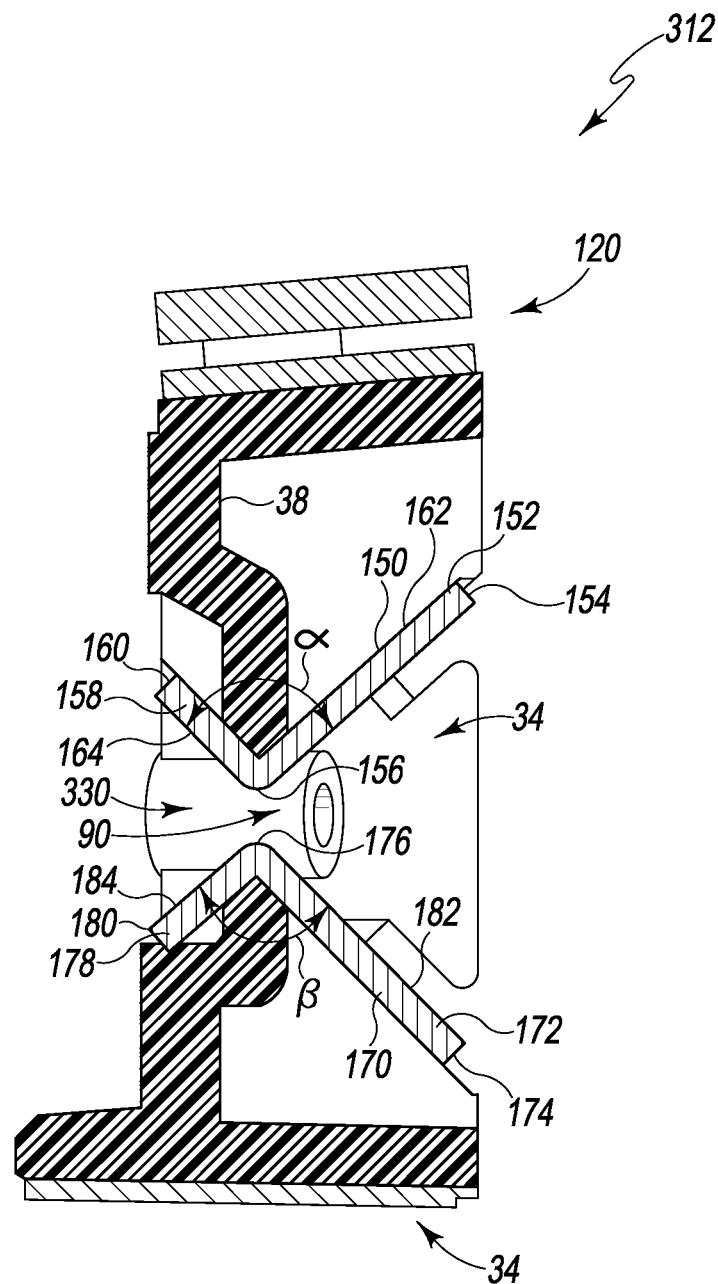
FIG. 16 is a cross section view of the orthopaedic surgical instrument, taken along the line 16-16 in FIG. 14, as viewed in the direction of the arrows.

As shown in FIG. 16, the inner end 156 defines an apex of the metallic body 150. The inner end 176 is positioned opposite the inner end 156 and defines an apex of the metallic body 170. An opening 190 sized to receive the saw blade 96 is defined between the inner ends 156, 176 of the bodies 150, 170.

In the illustrative embodiment, the metallic planar cutting guide 132 of the chamfer cutting guide assembly 330 is defined by the plate 152 of the body 150 and the plate 178 of the body 170. As shown in FIG. 16, the end 154 of the body 150 defines the anterior end of the metallic planar cutting guide 132 and the end 180 of the body 170 defines the posterior end of the metallic planar cutting guide 132. The plates 152, 178 (and hence the planar surfaces 162, 184) of the metallic planar cutting guide 132 are spaced apart, and extend parallel to, each other, and the plates 152, 178 cooperate to guide the saw blade 96 during the performance of an anterior chamfer cut.

As described above, the chamfer cutting guide assembly 330 also includes a metallic planar cutting guide 134 that extends at an oblique angle relative to the metallic planar cutting guide 132. The metallic planar cutting guide 134 is defined by the plate 158 of the body 150 and the plate 172 of the body 170. As shown in FIG. 16, the end 160 of the body 150 defines the anterior end of the metallic planar cutting guide 134 and the end 174 of the body 170 defines the posterior end of the metallic planar cutting guide 134. The plates 158, 172 (and hence the planar surfaces 164, 182) of the metallic planar cutting guide 134 are spaced apart, and extend parallel to, each other, and the plates 158, 172 cooperate to guide the saw blade 96 during the performance of a posterior chamfer cut.

The medial and lateral ends of the chamfer cutting guide assembly 330 are defined by a pair of metallic bushings 356, 358. In particular, the metallic bushing 356 is positioned in an enlarged cylindrically-shaped medial end of the chamfer cutting slot 36—that is, the metallic bushing 356 is secured in contact with the medial edge 44 of the sidewall 38 defining the medial end of the chamfer cutting slot 36. The metallic bushing 358 is positioned in an enlarged cylindrically-shaped lateral end of the chamfer cutting slot 36—that is, the metallic bushing 358 is secured in contact with the lateral edge 46 of the sidewall 38 defining the lateral end of the chamfer cutting slot 36.

Figure 14:
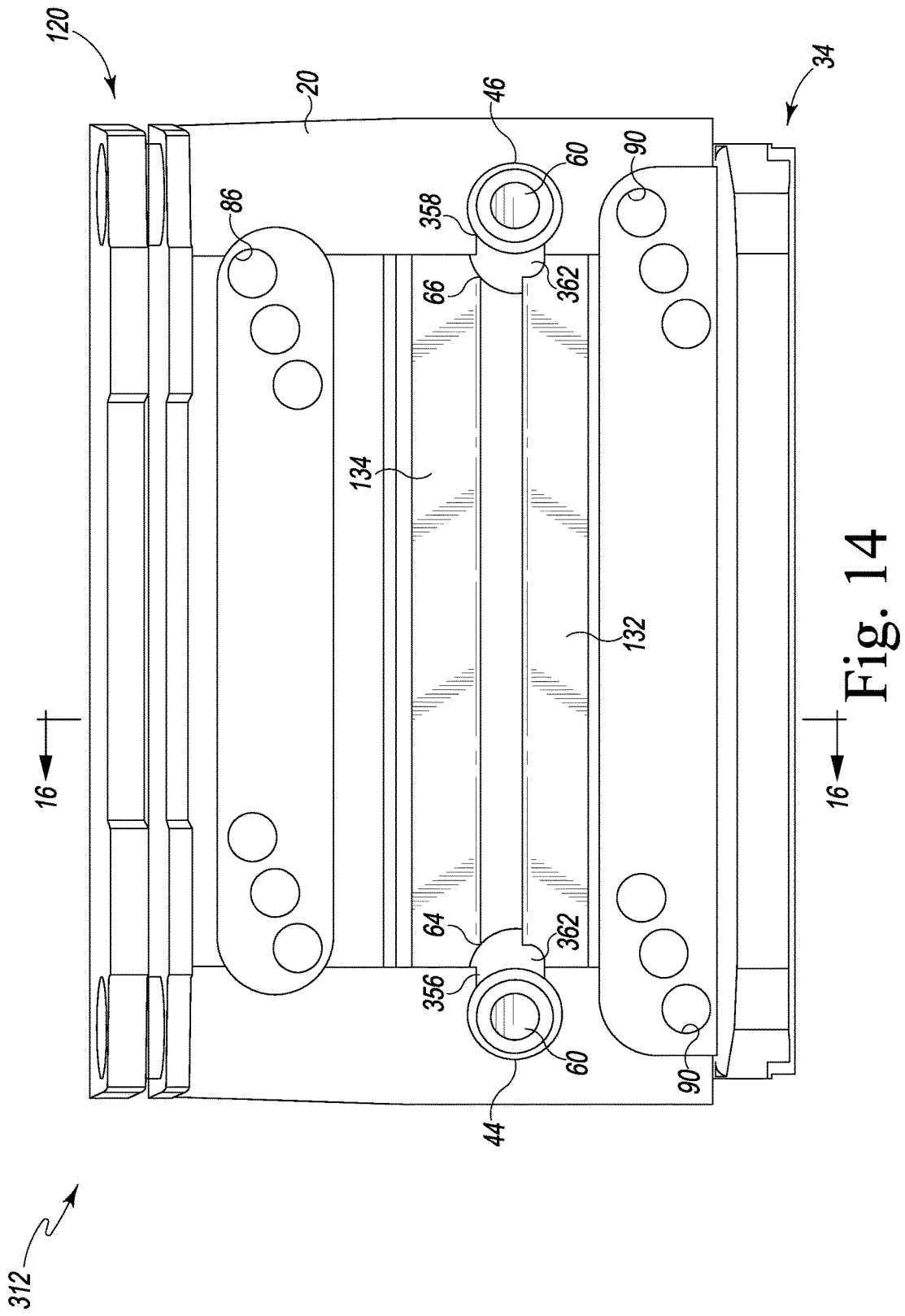
FIG. 14 is a front elevation view of the orthopaedic surgical instrument of FIG. 13.
Figure 15:
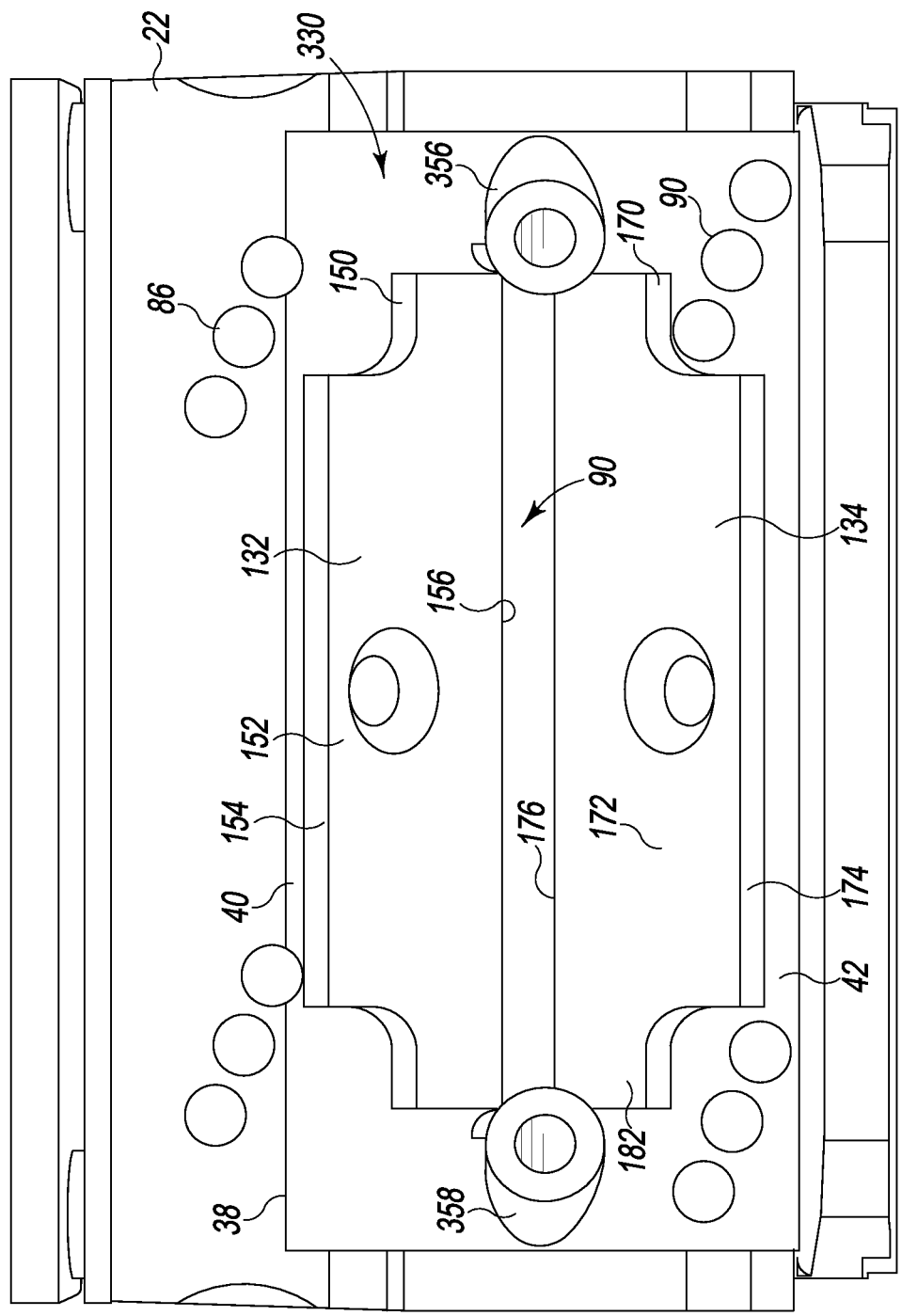
FIG. 15 is a rear elevation view of the orthopaedic surgical instrument of FIG. 13.

The metallic bushings 356, 358 are cylindrically-shaped and have an elongated bore 60 extending therethrough. The elongated bore 60 is sized to receive a fixation or guide pin for pinning the 4-in-1 cutting block to the patient's distal femur, and, optionally, a drill such that the patient's femur may be pre-drilled prior to installation of the guide pins if the surgeon so desires. The metallic bushings 356, 358 are identical in shape and include an annularly-shaped outer surface 362. As can be seen in FIG. 14, the outer surface 362 of the metallic bushing 356 is positioned at the medial end 64 of the planar cutting guides 132, 134, with the outer surface 62 of the metallic bushing 58 being positioned at the lateral end 66 of the planar cutting guides 132, 134. In the illustrative embodiment described herein, the outer surface 362 of the metallic bushings 356, 358 is in contact with the respective medial end 64 and lateral end 66 of the planar cutting guides 132, 134 (i.e., the bushings 356, 358 are positioned in contact with the planar cutting guides 132, 134).

In operation, the surgeon may attach the cutting block 312 to the patient's femur 100 in a manner similar to that described above in regard to the cutting blocks 12, 112. Once attached, the surgeon may also use the planar cutting guides 132, 134 to make chamfer cuts on the patient's femur 100. To do so, the surgeon may first insert fixation pins 88 through the elongated bores 60 of the metallic bushings 356, 358 of the chamfer cutting guides assembly 50. The surgeon may then remove any fixation pins 88 from the guide holes 86, 90 since fixation pins 88 positioned in the guide holes 86, 90 would disrupt the chamfer cutting process.

The surgeon may then advance the surgical cutting saw 96 through the opening 190 defined between the metallic bodies 150, 170 to guide the saw blade 96 during the performance of the anterior chamfer cut. As the saw blade 96 makes the cut, the saw blade 96 engages the surfaces 162, 184 of the cutting guide 132. Similarly, the surgeon may advance the surgical cutting saw 96 through opening 190 defined between the metallic bodies 150, 170 to guide the saw blade 96 during the performance of the posterior chamfer cut. As the saw blade 96 makes the cut, the saw blade 96 engages the surfaces 164, 182 of the cutting guide 134.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

For example, although use of the metallic bushings 56, 58 as saw stops has herein been described in the illustrative example of a 4-in-1 block, it should be appreciated that other orthopaedic instruments may also be embodied with such a concept. For example, other orthopaedic cutting blocks may be so embodied. Additionally, it should be appreciated that in other embodiments the metallic bushings may be omitted from any of the cutting guide assemblies described above.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument comprising:
a polymer 4-in-1 femoral cutting block having a bone-engaging surface and an outer surface opposite the bone-engaging surface,
a chamfer cutting slot defined in the polymer 4-in-1 femoral cutting block, the chamfer cutting slot extending from a first opening defined in the outer surface to a second opening defined in the bone-engaging surface,
a first metallic planar cutting guide secured within the chamfer cutting slot, the first metallic planar cutting guide being defined by (i) a first planar surface and (ii) a second planar surface spaced apart from, and extending parallel to, the first planar surface, the first and second planar surfaces extending from a lateral end to a medial end of the first metallic planar cutting guide,
a second metallic planar cutting guide secured within the chamfer cutting slot, the second metallic planar cutting guide being defined by (i) a third planar surface extending at an oblique angle relative to the first planar surface, and (ii) a fourth planar surface extending parallel to, spaced apart from, the third planar surface, the third and fourth planar surfaces extending from a lateral end to a medial end of the second metallic planar cutting guide,
a first metallic bushing secured within the chamfer cutting slot of the polymer 4-in-1 femoral cutting block, the first metallic bushing extending from the first opening of the chamfer cutting slot defined in the outer surface toward the second opening of the chamfer cutting slot defined in the bone-engaging surface, an outer surface of the first metallic bushing being positioned at the lateral end of each of the first and second metallic planar cutting guides, and
a second metallic bushing secured within the chamfer cutting slot of the polymer 4-in-1 femoral cutting block, the second metallic bushing extending from the first opening of the chamfer cutting slot defined in the outer surface toward the second opening of the chamfer cutting slot defined in the bone-engaging surface, an outer surface of the second metallic bushing being positioned at the medial end of each of the first and second metallic planar cutting guides.

2. The orthopaedic surgical instrument of claim 1, wherein:
the fourth planar surface is connected to, and extends at an oblique angle relative to, the first planar surface, and
the second planar surface is connected to, and extends at an oblique angle relative to, the third planar surface.

3. The orthopaedic surgical instrument of claim 1, wherein the first planar surface is spaced apart from the third planar surface in an anterior/posterior direction.

4. The orthopaedic surgical instrument of claim 1, further comprising:
a third metallic planar cutting guide secured within the chamfer cutting slot of the polymer 4-in-1 femoral cutting block, and
a fourth metallic planar cutting guide secured within the chamfer cutting slot of the polymer 4-in-1 femoral cutting block, the fourth metallic planar cutting guide being arranged at an oblique angle relative to the third metallic planar cutting guide.

5. The orthopaedic surgical instrument of claim 4, wherein the third metallic planar cutting guide extends parallel to the first metallic planar cutting guide, and the fourth metallic planar cutting guide extends parallel to the second metallic planar cutting guide.

6. The orthopaedic surgical instrument of claim 1, wherein the polymer 4-in-1 femoral cutting block further has an anterior cutting slot defined therein, the anterior cutting slot being spaced apart anteriorly from the chamfer cutting slot, the orthopaedic surgical instrument further comprising a metallic anterior cutting guide secured within the anterior cutting slot of the polymer 4-in-1 femoral cutting block.

7. The orthopaedic surgical instrument of claim 6, wherein the polymer 4-in-1 femoral cutting block further has a posterior cut surface defined therein, the posterior cut surface being spaced apart posteriorly from the chamfer cutting slot, the orthopaedic surgical instrument further comprising a metallic posterior cutting guide secured to the posterior cut surface of the polymer 4-in-1 femoral cutting block.

8. The orthopaedic surgical instrument of claim 1, wherein the first metallic bushing is secured within an enlarged cylindrically-shaped lateral end of the chamfer cutting slot, and the second metallic bushing is secured within an enlarged cylindrically-shaped medial end of the chamfer cutting slot.

9. An orthopaedic surgical instrument comprising:
a polymer 4-in-1 femoral cutting block having a bone-engaging surface and an outer surface opposite the bone-engaging surface,
a chamfer cutting slot defined in the polymer 4-in-1 femoral cutting block, the chamfer cutting slot extending from a first opening defined in the outer surface to a second opening defined in the bone-engaging surface,
first and second metallic bushings secured within the chamfer cutting slot of the polymer 4-in-1 femoral cutting block and extending from the first opening of the chamfer cutting slot defined in the outer surface toward the second opening of the chamfer cutting slot defined in the bone-engaging surface, and
a metallic chamfer cutting guide assembly secured within the chamfer cutting slot, the chamfer cutting guide assembly comprising: (i) a first planar surface, (ii) a second planar surface spaced apart from, and extending parallel to, the first planar surface, (iii) a third planar surface connected to the second planar surface and extending at an oblique angle relative to the first planar surface and (iv) a fourth planar surface connected to the first planar surface and extending parallel to the third planar surface,
wherein the first planar surface and the second planar surface define a first metallic planar cutting guide, and the third planar surface and the fourth planar surface define a second metallic planar cutting guide arranged at an oblique angle relative to, and spaced apart from, the first metallic planar cutting guide.

10. The orthopaedic surgical instrument of claim 9, further comprising the first metallic bushing having an outer surface thereof positioned at a lateral end of each of the first and second metallic planar cutting guides, and the second metallic bushing having an outer surface thereof positioned at a medial end of each of the first and second metallic planar cutting guides.

11. The orthopaedic surgical instrument of claim 10, wherein:
the outer surface of the first metallic bushing is spaced apart laterally from the lateral ends of the first and second metallic planar cutting guides, and
the outer surface of the second metallic bushing is spaced apart medially from the medial ends of the first and second metallic planar cutting guides.

12. The orthopaedic surgical instrument of claim 10, wherein each of the first and second metallic bushings comprises a cylindrically-shaped bushing having an elongated bore extending therethrough.

13. The orthopaedic surgical instrument of claim 9, wherein the first planar surface is spaced apart from the third planar surface in an anterior/posterior direction.

14. The orthopaedic surgical instrument of claim 9, wherein the chamfer cutting guide assembly further includes a fifth planar surface positioned opposite the first planar surface in the chamfer cutting slot of the polymer 4-in-1 femoral cutting block, the fifth planar surface being spaced apart from, and extending parallel relative to, the first planar surface such that the first planar surface, the second planar surface, and the fifth planar surface define the first metallic planar cutting guide.

15. The orthopaedic surgical instrument of claim 14, wherein the chamfer cutting guide assembly further includes a sixth planar surface positioned opposite the third planar surface in the chamfer cutting slot of the polymer 4-in-1 femoral cutting block, the sixth planar surface being spaced apart from, and extending parallel relative to, the third planar surface such that the third planar surface, the fourth planar surface, and the sixth planar surface define the second metallic planar cutting guide.

16. The orthopaedic surgical instrument of claim 9, wherein the first metallic bushing is secured within an enlarged cylindrically-shaped lateral end of the chamfer cutting slot, and the second metallic bushing is secured within an enlarged cylindrically-shaped medial end of the chamfer cutting slot.

17. An orthopaedic surgical instrument comprising:
a polymer 4-in-1 femoral cutting block having a bone-engaging surface and an outer surface opposite the bone-engaging surface,
a chamfer cutting slot defined in the polymer 4-in-1 femoral cutting block, the chamfer cutting slot extending from a first opening defined in the outer surface to a second opening defined in the bone-engaging surface,
first and second metallic bushings secured within the chamfer cutting slot of the polymer 4-in-1 femoral cutting block and extending from the first opening of the chamfer cutting slot defined in the outer surface toward the second opening of the chamfer cutting slot defined in the bone-engaging surface,
a first metallic planar cutting guide secured within the chamfer cutting slot, the first metallic planar cutting guide extending through the chamfer cutting slot from a first end to a second end, and
a second metallic planar cutting guide secured within the chamfer cutting slot, the second metallic planar cutting guide being arranged at an oblique angle relative to, and spaced apart from, the first metallic planar cutting guide and extending from a first end positioned posterior of the first end of the first metallic planar cutting guide to a second end positioned anterior of the second end of the first metallic planar cutting guide,
wherein the first metallic planar cutting guide is defined by (i) a first metallic plate extending from the first end of the first metallic planar cutting guide to an inner end and (ii) a second metallic plate extending parallel to the first metallic plate and inwardly from the second end of the first metallic planar cutting guide to an inner end spaced apart from the inner end of the first metallic plate, and
wherein the second metallic planar cutting guide is defined by a third metallic plate connected to the inner end of the second metallic plate, the third metallic plate extending from the inner end of the second metallic plate to the first end of the second metallic planar cutting guide.

18. The orthopaedic surgical instrument of claim 17, wherein the second metallic planar cutting guide is further defined by a fourth metallic plate connected to the inner end of the first metallic plate and extending outwardly, parallel to the third metallic plate, to the second end of the second metallic planar cutting guide.

19. The orthopaedic surgical instrument of claim 18, wherein:
the first metallic planar cutting guide is further defined by a fifth metallic plate extending parallel to, and spaced apart from, the first metallic plate and the second metallic plate, and
the second metallic planar cutting guide is further defined by a sixth metallic plate extending parallel to, and spaced apart from, the third metallic plate and the fourth metallic plate.

20. The orthopaedic surgical instrument of claim 17, wherein the first metallic bushing is secured within an enlarged cylindrically-shaped lateral end of the chamfer cutting slot, and the second metallic bushing is secured within an enlarged cylindrically-shaped medial end of the chamfer cutting slot.

* * * * *